United States Patent
Dilley et al.

(10) Patent No.: US 7,029,888 B2
(45) Date of Patent: Apr. 18, 2006

(54) MODIFIED SYNTHETASES TO PRODUCE PENICILLINS AND CEPHALOSPORINS UNDER THE CONTROL OF BICARBONATE

(75) Inventors: David R. Dilley, East Lansing, MI (US); Dina K. Kadyrzhanova, East Lansing, MI (US); Zhenyong Wang, Okemos, MI (US); Toni M. Warner, Fredericksburg, VA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 612 days.

(21) Appl. No.: 09/924,841

(22) Filed: Aug. 8, 2001

(65) Prior Publication Data

US 2002/0127633 A1   Sep. 12, 2002

Related U.S. Application Data

(62) Division of application No. 09/413,231, filed on Oct. 6, 1999, now Pat. No. 6,284,483.

(51) Int. Cl.
| | |
|---|---|
| *C12N 9/02* | (2006.01) |
| *C12N 1/20* | (2006.01) |
| *C12N 1/14* | (2006.01) |
| *C12N 15/00* | (2006.01) |
| *C07H 21/04* | (2006.01) |

(52) U.S. Cl. .............. 435/189; 435/4; 435/6; 435/252.3; 435/254.3; 435/320.1; 435/440; 536/23.2; 536/23.74

(58) Field of Classification Search ................ 435/193, 435/252.3, 320.1, 69.1, 71.1, 440, 6, 189, 435/254.21, 255.2, 254.11, 148, 4, 254.3; 536/23.2, 23.74

See application file for complete search history.

(56) References Cited

U.S. PATENT DOCUMENTS 4,885,251 A   12/1989 Ingolia et al.

(Continued)

OTHER PUBLICATIONS

Perry et al., Biochem. J. 255:345-351 (1988).

(Continued)

Primary Examiner—Manjunath Rao
Assistant Examiner—Yong Pak
(74) Attorney, Agent, or Firm—Ian C. McLeod

(57) ABSTRACT

The present invention relates to a modified enzyme of a non-heme iron (II) dependent family of oxygenases and oxidases which renders the enzyme dependent on bicarbonate for activity. In a preferred embodiment, the modification is an arginine, lysine, or other amino acid that is two amino acid residues upstream of a histidine residue that is an iron ligand in the enzyme and is one of the histidine residues of the 2-histidine-1-aspartic acid trifacial motif. In particular, the modified enzymes are isopenicillin N synthetase, deacetoxycephalosporin C synthetase, and deacetoxycephalosporin C synthetase/deacetylcephalosporin C synthetase which are used to make antibiotics. The present invention further provides a method for making antibiotics using a modified enzyme such as isopenicillin N synthetase, deacetoxycephalosporin C synthetase, and deacetoxycephalosporin C synthetase/deacetylcephalosporin C synthetase wherein the modification renders the enzyme dependent on bicarbonate for activity. Finally, the present invention provides a method for making antibiotics by providing the modified enzyme either in either an organism or in a cell-free system.

3 Claims, 2 Drawing Sheets

U.S. PATENT DOCUMENTS

| | | | |
|---|---|---|---|
| 4,885,252 A | 12/1989 | Ingolia et al. |
| 4,892,819 A | 1/1990 | Carr et al. |
| 4,950,603 A | 8/1990 | Ingolia et al. |
| 5,070,020 A | 12/1991 | Ingolia et al. |
| 5,462,862 A | 10/1995 | Groenen et al. |
| 5,753,435 A | 5/1998 | Aharonowitz et al. |
| 5,882,879 A | 3/1999 | Veenstra et al. |
| 5,882,883 A | 3/1999 | Egel-Mitani et al. |
| 5,919,680 A | 7/1999 | Sutherland et al. |
| 5,942,411 A | 8/1999 | Kaasgaard et al. |

OTHER PUBLICATIONS

Zhang et al. Biochem. 36:15999-16007 (1997).

Kadyrzhanova et al. in Biology and Biotechnology of the Plant Hormone Ethylene (1997).

Kanellis et al, (eds.), Kluwer Academic Publishers, Netherlands, pp. 5-13.

Hegg and Que, Eur. J. Biochem. 250:625-629 (1997).

Campbell et al. in Curr. Genet. 16:53-56 (1989).

Bird and Bradshaw in Mol. Gen.Genet. 255:219-225 (1997).

Sanchez et al. in Mol. Gen. Genet. 258:89-94 (1998).

Sambrook et al. (eds.) Molecular Cloning: A Laboratory Manual, Second Ed. Cold Spring Harbor Lab. Press (1989).

Hsiung et al., Nuc. Acid Res. 11:3227 (1983).

Narang et al., Methods in Enzymology 68: 90 (1979).

Wiegel et al., J. Bacteriol. 170:3817-3826 (1988).

Deng and Nickoloff, Anal. Biochem. 200:81-88 (1992).

| Organism | Amino Acid Sequence Flanking the Histidine that is the Iron Ligand | |
|---|---|---|
| 1. E. nidulans | ...DGTKLSFEWHEDVSLITVLYQ... | (a.a. 205 - 225) |
| 2. P. chrysogenum | ...DGTKLSFEWHEDVSLITVLYQ... | (a.a. 205 - 225) |
| 3. A. chrysogenum | ...DGTKLSFEWHEDVSLITVLYQ... | (a.a. 207 - 227) |
| 4. S. clavuligerus | ...DGQLLSFEDHLDVSMITVLFQ... | (a.a. 203 - 223) |
| 5. S. cattleya | ...DGTRLSFEDHLDVSMITVLSE... | (a.a. 204 - 224) |
| 6. S. anulatus | ...DGTRLSFEDHLDVSMITVLFQ... | (a.a. 207 - 227) |
| Consensus | DG--LSFE-H-DVS-ITVL-- | |

MODIFIED SYNTHETASES TO PRODUCE PENICILLINS AND CEPHALOSPORINS UNDER THE CONTROL OF BICARBONATE

CROSS-REFERENCE TO RELATED APPLICATION

This application is a divisional of Ser. No. 09/413,231 filed Oct. 6, 1999, now issued as U.S. Pat. No. 6,284,483.

STATEMENT REGARDING FEDERALLY SPONSORED RESEARCH OR DEVELOPMENT

None.

BACKGROUND OF THE INVENTION (1) Field of the Invention

The present invention relates to a modified enzyme of a non-heme iron (II) dependent family of oxygenases and oxidases which renders the enzyme dependent on bicarbonate for activity. In a preferred embodiment, the modification is an arginine, lysine, or other amino acid that is two amino acid residues upstream of a histidine residue that is an iron ligand in the enzyme and is one of the histidine residues of the 2-histidine-1-aspartic acid trifacial motif. In particular, the present invention relates to isopenicillin N synthetase (IPNS), deacetoxycephalosporin C synthetase (DAOCS), and deacetoxycephalosporin C synthetase/deacetylcephalosporin C synthetase (DAOCS/DACS) which are modified to be dependent on bicarbonate for activity. The present invention further relates to organisms that express IPNS and/or DAOCS or DAOCS/DACS having activity dependent on bicarbonate. Finally, the present invention relates to in vivo and in vitro methods for producing antibiotics wherein production is dependent on bicarbonate.

(2) Description of Related Art

β-lactam antibiotics are the largest group of secondary metabolites produced by microorganisms. The penicillins (penam) and cephalosporins (cepham) are the most important of these β-lactams from both a clinical and an economic standpoint. The biosynthesis of these β-lactams occurs by a complex series of enzymatic steps with the first two steps being key for both the biosynthesis of penams and cephams. Afterwards, the pathway for the biosynthesis of penicillins and cephalosporins diverge. The key steps in the biosynthesis of penicillins and cephalosporins are shown in FIG. 1.

The first step in the formation of penams and cephams is the condensation of L-α-amino adipic acid (A), L-cysteine (C), and L-valine (V) by ACV synthetase to form the tripeptide δ-(L-α-aminoadipyl)-L-cysteinyl-D-valine (ACV). In the second step, the tripeptide is cyclized in a four electron oxidation of ACV by molecular oxygen catalyzed by isopenicillin synthetase (IPNS) to produce isopenicillin N. IPNS requires dioxygen to form the ferryl form of the enzyme which catalyzes the cyclization reaction. Isopenicillin N contains a β-lactam and thiazolidine ring structure and possess antibacterial activity. To form penicillin G or V, the α-aminoadipic acid side chain of isopenicillin N is exchanged for phenyacetic acid to yield penicillin G or phenoxyacetic acid to yield penicillin V. This reaction is catalyzed by acetyltransferase.

To make the cephams, the A chain of isopenicillin N is racemized in a reaction catalyzed by an epimerase or racemase to form penicillin N. Then the five-member thiazolidine ring in penicillin N is expanded into the six-member dihydrothiazine ring of the cephalosporin nucleus by deacetoxycephalosporin C synthetase/deacetylcephalosporin C synthetase (DAOCS/DACS) or expandase. The reaction requires dioxygen and 2-oxoglutarate (α-ketogluterate) to produce the ferryl form of the enzyme. The same enzyme also catalyzes the subsequent reaction in the pathway which is the hydroxylation of the methyl group at the 3'-position of the ring to form deacetylcephalosporin C. In prokaryotes such as Streptomyces, the deacetoxycephalosporin C synthetase (DAOCS) and deacetylcephalosporin C synthetase (DACS) are encoded by separate genes; however, the prokaryote and eukaryote enzymes are closely related by amino acid sequence. Cephalosporin C is formed from deacetylcephalosporin C by acetylation of the 3'-position. The cephamycins are then formed in several subsequent enzymatic steps.

In the commercial production of antibiotics, a primary concern has been directed towards improving the yield of penams and cephams. Improving the yields in vivo have been achieved primarily by increasing the copy number of IPNS, DAOCS, or DAOCS/DACS or other ancillary enzymes which appear to improve the yield of the penam or cepham in the organism. Other methods for improving yields has been directed towards development of in vitro systems based on the enzymes involved in the biosynthesis of penams and cephams.

The following U.S. Patents disclose methods for improving yields of penams and cephams, both in vivo and in vitro.

U.S. Pat. No. 4,885,251 to Ingolia et al. discloses DNAs encoding IPNS and its flanking regulatory sequences from Cephalosporin acremonium. The isolated gene was used to make novel E. coli expression vectors that drive production of isopenicillin N synthetase in E. coli.

U.S. Pat. No. 4,885,252 to Ingolia et al. discloses DNAs encoding IPNS from Aspergillus nidulans and its use in the production of β-lactams. In particular, the gene encoding the synthetase can be isolated from plasmid pOGOO4, available from the Northern Regional Research Center under accession number NRRL B-18171.

U.S. Pat. No. 4,892,819 to Carr et al. discloses DNAs containing a gene encoding IPNS and its flanking regulatory sequences from Penicillin chrysogenum. The gene was used to make novel E. coli expression vectors that drive production of IPNS in E. coli.

U.S. Pat. No. 4,950,603 to Ingolia et al. discloses DNAs containing a gene encoding IPNS from Streptomyces lipmanii, a plasmid pOGO239 containing the gene as NRRL B-18250, and methods for using the gene encoding the synthetase in the production of antibiotics.

U.S. Pat. No. 5,070,020 to Ignolia et al. discloses DNAs containing genes encoding DAOCS activity, recombinant DNA vectors containing the synthetase for expression in a wide variety of host organisms, including E. coli, Penicillium, Streptomyces, Aspergillus, and Cephalosporin.

U.S. Pat. No. 5,462,862 to Groenen et al. discloses DNAs containing genes encoding IPNS, acetyltransferase, and ACV synthetase and transforming host organisms with these DNAs to improve production of an antibiotic. Improvement of production is by increased copy number of the gene in the transformed organism.

U.S. Pat. No. 5,753,435 to Aharonowitz et al. discloses DNAs containing a gene encoding a new oxido reductase activity obtainable from Penicillium chrysogenum involved in the production of β-lactams and provides methods for using the oxido reductase to improve production of β-lactams.

U.S. Pat. No. 5,882,879 to Veenstra et al. discloses DNAs containing genes encoding the ACV synthetase genes from Penicillium chrysogenum and Acremonium chrysogenum, and methods for using clones of the genes to improve antibiotic biosynthesis.

U.S. Pat. No. 5,882,883 to Egel-Mitani et al. provides an improved process for making an antibiotic in a fermentation process by placing a gene encoding a key enzyme in the biosynthesis process under the control of a heterologous promoter which enables the transcription of the gene to be regulatable. This improvement avoids inhibition of transcription of the enzyme by secondary metabolites formed during the synthesis of the antibiotic.

U.S. Pat. No. 5,942,411 to Kaasgaard et al. discloses a method for improving the production of various β-lactam antibiotics in vivo and in vitro by inducing the host organism to express an increased ligase activity, in particular an acetyl-coenzyme A synthetase (ligase).

Other efforts have been directed towards modifying the substrate specificity of expandase to enable biosynthesis of intermediates such as 7-aminodesacetoxycephalosporanic acid (7-ADCA) that can be used in subsequent reactions to make semi-synthetic cephalosporins. For example, U.S. Pat. No. 5,919,680 to Sutherland et al. discloses a process for preparation and recovery of 7-ADCA using a Penicillium chrysogenum transformant expressing a modified expandase that is able to use penicillin G as its substrate.

While the prior art provides methods for improving production of antibiotics by a variety of genetic engineering methods, the prior art has not provided or suggested any means which would enable the activity of an antibiotic biosynthesis enzyme such as IPNS to be dependent on the presence of an activating compound.

SUMMARY OF THE INVENTION

The present invention relates to a modified enzyme of a non-heme iron (II) dependent family of oxygenases and oxidases which renders the enzyme dependent on bicarbonate for activity and wherein the modification is an amino acid such as an arginine or lysine residue that is two amino acid residues upstream of a histidine residue that is an iron ligand in the enzyme and is one of the histidine residues of the 2-histidine-1-aspartic acid trifacial motif. In particular, the modified enzymes are isopenicillin N synthetase, deacetoxycephalosporin C synthetase, and deacetoxycephalosporin C synthetase/deacetylcephalosporin C synthetase which are used to make antibiotics. The present invention further provides a method for making antibiotics using a modified enzyme such as isopenicillin N synthetase, deacetoxycephalosporin C synthetase, and deacetoxycephalosporin C synthetase/deacetylcephalosporin C synthetase wherein the modification renders the enzyme dependent on bicarbonate for activity. Finally, the present invention provides a method for making antibiotics by providing the modified enzyme either in either an organism or in a cell-free system.

Thus, the present invention provides a modified organism for producing an antibiotic, comprising a mutation in a gene encoding an enzyme of a non-heme iron (II) dependent family of oxygenases and oxidases wherein the mutation renders the enzyme dependent on bicarbonate as an activator to produce the antibiotic. In particular, the modified organism wherein the mutation is the amino acid residue two amino acid residues upstream of a histidine residue which is an iron ligand of the enzyme wherein the mutation renders the enzyme dependent on bicarbonate as an activator to produce the antibiotic. In a preferred embodiment, the amino acid residue two amino acid residues upstream of the histidine in the enzyme is an arginine or a lysine.

In particular, the present invention provides a modified or genetically engineered organism for producing an antibiotic that is dependent on bicarbonate, comprising a mutation in the gene encoding an enzyme of a non-heme iron (II) dependent family of oxygenases and oxidases wherein the mutation produces the enzyme that has an arginine residue two amino acid residues upstream of a histidine residue which is an iron ligand of the enzyme wherein the mutation renders the enzyme dependent on bicarbonate as an activator to produce the antibiotic.

In a first species, the present invention provides a modified organism for producing penicillin, which comprises a mutation in a gene encoding an isopenicillin N synthetase (IPNS) activity wherein the mutation produces the IPNS that has an amino acid such as an arginine or lysine residue at a position two amino acid residues upstream of a histidine residue which is an iron ligand of the IPNS wherein the mutation renders the IPNS dependent on bicarbonate as an activator to produce the penicillin.

In a second species, the present invention provides a modified organism for producing cephalosporin C, which comprises a mutation in a gene encoding a deacetoxycephalosporin C synthetase (DAOCS) activity wherein the mutation produces the DAOCS that has an amino acid such as an arginine or lysine residue at a position two amino acid residues upstream of a histidine residue which is an iron ligand of the DAOCS wherein the mutation renders the DAOCS dependent on bicarbonate as an activator to produce the cephalosporin C.

In a third species, the present invention provides a modified organism for producing cephalosporin C, which comprises a mutation in a gene encoding a deacetoxycephalosporin C synthetase/deacetylcephalosporin C synthetase (DAOCS/DACS) activity wherein the mutation produces the DAOCS/DACS that has an amino acid such as an arginine or lysine residue at a position two amino acid residues upstream of a histidine residue which is an iron ligand of the DAOCS/DACS wherein the mutation renders the DAOCS/DACS dependent on bicarbonate as an activator to produce the cephalosporin C.

The present invention further provides an isolated DNA encoding an enzyme of a non-heme iron (II) dependent family of oxygenases and oxidases useful for the synthesis of an antibiotic wherein the isolated DNA comprises a codon that is two codons upstream of a histidine codon which is an iron ligand of the enzyme has been modified to encode an amino acid that renders the enzyme dependent on bicarbonate as an activator of the enzyme. In a preferred embodiment, the amino acid residue two amino acid residues upstream of the histidine in the enzyme is an arginine or a lysine.

In particular, the present invention provides an isolated DNA encoding an enzyme of a non-heme iron (II) dependent family of oxygenases and oxidases useful for the synthesis of an antibiotic wherein the isolated DNA comprises a codon that has been modified to encode an amino acid such as an arginine or lysine which is two codons upstream of a histidine codon which is an iron ligand of the enzyme wherein the amino acid renders the enzyme dependent on bicarbonate as an activator of the enzyme.

In a first species, the present invention provides an isolated DNA encoding an isopenicillin N synthetase (IPNS) activity wherein the isolated DNA comprises a codon that has been modified to encode an amino acid such as an arginine or lysine which is two codons upstream from the codon that encodes a histidine residue which is an iron ligand of the IPNS wherein the amino acid renders the IPNS dependent on bicarbonate as an activator of the IPNS.

In a second species, the present invention provides an isolated DNA encoding a deacetoxycephalosporin C synthetase (DAOCS) activity wherein the isolated DNA comprises a codon that has been modified to encode an amino acid such as an arginine or lysine which is two codons upstream from the codon that encodes a histidine residue which is an iron ligand of the DAOCS wherein the amino acid renders the DAOCS dependent on bicarbonate as an activator of the DAOCS.

In a third species, the present invention provides an isolated DNA encoding a deacetoxycephalosporin C synthetase/deacetylcephalosporin C synthetase (DAOCS/DACS) activity wherein the isolated DNA comprises a codon that has been modified to encode an amino acid such as an arginine or lysine which is two codons upstream from the codon that encodes a histidine residue which is an iron ligand of the (DAOCS/DACS) wherein the amino acid renders the (DAOCS/DACS) dependent on bicarbonate as an activator of the (DAOCS/DACS).

The present invention further provides an enzyme of a non-heme iron (II) dependent family of oxygenases and oxidases which is in a pathway to produce an antibiotic, comprising a mutation which is an amino acid residue that is two amino acid residues upstream of a histidine residue which is an iron ligand of the enzyme wherein the mutation renders the enzyme dependent on bicarbonate to produce the antibiotic. In a preferred embodiment, the amino acid that is two amino acid residues upstream of the histidine is an arginine or a lysine.

In particular, the present invention provides an isopenicillin N synthetase (IPNS) to produce penicillin, comprising a mutation wherein the mutation is an amino acid residue such as an arginine or lysine at a position two amino acid residues upstream of a histidine residue which is an iron ligand of the IPNS wherein the mutation renders the IPNS dependent on bicarbonate as an activator to produce the penicillin.

The present invention further provides a deacetoxycephalosporin C synthetase (DAOCS) to produce cephalosporin C, comprising a mutation wherein the mutation is an amino acid residue such as an arginine or lysine at a position two amino acid residues upstream of a histidine residue which is an iron ligand of the DAOCS wherein the mutation renders the DAOCS dependent on bicarbonate as an activator to produce the cephalosporin C.

Further still, the present invention provides a deacetoxycephalosporin C synthetase/deacetylcephalosporin C synthetase (DAOCS/DACS) to produce cephalosporin C, comprising a mutation wherein the mutation is an amino acid residue such as an arginine or lysine at a position two amino acid residues upstream of a histidine residue which is an iron ligand of the DAOCS/DACS wherein the mutation renders the DAOCS/DACS dependent on bicarbonate as an activator to produce the cephalosporin C.

The present invention also provides a method for producing an antibiotic, comprising: (a) providing an organism comprising a mutation in an enzyme of a non-heme iron (II) dependent family of oxygenases and oxidases which is in an antibiotic synthesis pathway to produce the antibiotic wherein the mutation is an amino acid residue that is two amino acid residues upstream of a histidine residue which is an iron ligand of the enzyme wherein the mutation renders the enzyme dependent on bicarbonate as an activator; (b) growing the organism in log phase in a culture without supplemental bicarbonate; (c) adding the bicarbonate to activate the enzyme; and (d) isolating the antibiotic produced by the antibiotic synthesis pathway. In a preferred embodiment, the amino acid residue two amino acid residues upstream of the histidine in the enzyme is an arginine or a lysine. In particular embodiments of the method, the enzyme that is modified is selected from the group consisting of isopenicillin N synthetase (IPNS), deacetoxycephalosporin C synthetase (DAOCS), and deacetoxycephalosporin C synthetase/deacetylcephalosporin C synthetase (DAOCS/DACS).

The present invention also provides a method for producing an antibiotic, comprising: (a) providing an organism comprising a mutation in an enzyme of a non-heme iron (II) dependent family of oxygenases and oxidases which is in an antibiotic synthesis pathway to produce the antibiotic wherein the mutation is an amino acid residue such as an arginine or lysine that is two amino acid residues upstream of a histidine residue which is an iron ligand of the enzyme wherein the mutation renders the enzyme dependent on bicarbonate as an activator; (b) growing the organism in log phase in a culture without supplemental bicarbonate; (c) adding the bicarbonate to activate the enzyme; and (d) isolating the antibiotic produced by the antibiotic synthesis pathway.

Thus, the present invention provides a method for producing penicillin G or V, comprising: (a) providing an organism comprising a mutation in an isopenicillin N synthetase (IPNS) wherein the mutation is an amino acid residue such as an arginine or lysine which is two amino acid residues upstream of a histidine residue which is an iron ligand of the IPNS wherein the mutation renders the IPNS dependent on bicarbonate as an activator; (b) growing the organism in log phase in a culture without supplemental bicarbonate; (c) adding the bicarbonate to activate the IPNS which converts δ-(L-α-aminoadipyl)-L-cysteinyl-D-valine to isopenicillin N; and (d) isolating the penicillin G or V which is produced from the isopenicillin N.

The present invention further provides a method for producing cephalosporin C, comprising: (a) providing an organism comprising a mutation in a synthetase selected from the group consisting of deacetoxycephalosporin C synthetase/deacetylcephalosporin C synthetase (DAOCS/DACS) and deacetoxycephalosporin C synthetase (DAOCS) wherein the mutation is an amino acid residue such as an arginine or lysine which is two amino acid residues upstream of a histidine residue which is an iron ligand of the synthetase wherein the mutation renders the synthetase dependent on bicarbonate as an activator; (b) growing the organism in log phase in a culture without supplemental bicarbonate; (c) adding the bicarbonate to activate the synthetase which converts isopenicillin N to cephalosporin C; and (d) isolating the cephalosporin C which is produced from the isopenicillin N.

The present invention further provides a method for producing cephalosporin C, comprising: (a) providing an organism comprising a mutation in a deacetoxycephalosporin c synthetase/deacetylcephalosporin C synthetase (DAOCS/DACS) wherein the mutation is an amino acid residue such as an arginine or lysine which is two amino acid residues upstream of a histidine residue which is an iron ligand of the DAOCS/DACS wherein the mutation renders the DAOCS/DACS dependent on bicarbonate as an activator; (b) growing the organism in log phase in a culture without supplemental bicarbonate; (c) adding the bicarbonate to activate the DAOCS/DACS which converts isopenicillin N to cephalosporin C; and (d) isolating the cephalosporin C which is produced from the isopenicillin N.

The present invention also provides a method for making production of an antibiotic by an enzyme of a non-heme iron (II) dependent family of oxygenases and oxidases dependant on bicarbonate for activating the enzyme comprising mutating a codon in a gene that encodes the enzyme to a codon that encodes an amino acid such as an arginine or lysine wherein the codon that is modified is two codons upstream from the codon that encodes a histidine which is an iron ligand of the enzyme wherein the mutation renders the production of the antibiotic dependent on the bicarbonate for activity. In particular, the enzyme is selected from the group consisting of isopenicillin N synthetase (IPNS), deacetoxycephalosporin C synthetase (DAOCS), and deacetoxycephalosporin C synthetase/deacetylcephalosporin C synthetase (DAOCS/DACS).

In all of the aforementioned aspects and embodiments of the present invention, the enzymes of the non-heme iron (II) dependent family of oxygenases and oxidases which are in an antibiotic synthesis pathway, such as IPNS, DAOCS, or DAOCS/DACS, are from an organism that belongs to a genus selected from the group comprising *Actinomycetes, Aspergillus, Bacillus, Cephalosporium, Cercospora, Escherichia, Eubacteria, Micromonospora, Nocardia, Penicillium, Pseudomonas, Streptomyces*, and filamentous fungi. In particular, the organism is a species selected from the group consisting of *Aspergillus nidulans, Cephalosporium acremonium, Penicillium chrysogenum, Acremonium chrysogenum, Emericella nidulans, Nocardia lactamdurans, Nocardia uniformus, Streptomyces antibioticus, Streptomyces anulatus, Streptomyces argenteolus, Streptomyces cattleya, Streptomyces chartreusis, Streptomyces clavuligerus, Streptomyces fimbriatus, Streptomyces flavovirens, Streptomyces flavus, Streptomyces fulvoviridis, Streptomyces griseus, Streptomyces halstedi, Streptomyces heteromorphus, Streptomyces hygroscopicus, Streptomyces lactamdurans, Streptomyces lipmanii, Streptomyces olivaceus, Streptomyces panayensis, Streptomyces pluracidomyceticus, Streptomyces rochei, Streptomyces sioyaensis, Streptomyces* sp. OA-6129, *Streptomyces* sp. KC-6643, *Streptomyces tokunomensis, Streptomyces viridochromogenes, Streptomyces wadayamensis, Agrobacterium, Gluconobacter*, and *Serratia*.

In particular, the present invention provides an IPNS activity wherein the IPNS activity comprises the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10 and a DAOCS activity has the sequence set forth in SEQ ID NO:18.

Therefore, it is an object of the present invention to provide a method for production of antibiotics by a modified enzyme of a non-heme iron (II) dependent family of oxygenases and oxidases wherein the mutation renders the enzyme dependent on bicarbonate for activity.

It is also an object to provide isopenicillin N synthetase, deacetoxycephalosporin C synthetase, and the bifunctional enzyme, deacetoxycephalosporin C synthetase/deacetylcephalosporin C synthetase which are dependant on bicarbonate for activity.

An object further still is to provide a method for making organisms useful for making an antibiotic dependent on bicarbonate to make the antibiotic.

DESCRIPTION OF THE DRAWINGS

FIG. 2 shows a comparison of the amino acid sequence relevant to the present invention from several organisms. The histidine residue (H) that is the iron binding ligand is in bold-faced type. For *E. nidulans*, amino acid sequence 205–225 from SEQ ID NO: 11 is shown; for *P. chrysogenum*, amino acid sequence 205–225 from SEQ ID NO:12 is shown; for *A. chrysogenum*, amino acid sequence 207–227 from SEQ ID NO:13 is shown; for *S. clavuligerus*, amino acid sequence 203–223 from SEQ ID NO:14 is shown; for *S. cattleya*, amino acid sequence 204–224 from SEQ ID NO:15 is shown; and, for *S. anulatus*, amino acid sequence 207–227 from SEQ ID NO:16 is shown. In FIG. 2, D is Aspartate, E is Glutamate, F is Phenylalanine, G is Glycine, I is isoleucine, K is Lysine, L is Leucine, Q is Glutamine, R is arginine, S is Serine, T is Threonine, V is Valine, and W is Tryptophan.

DESCRIPTION OF PREFERRED EMBODIMENTS

Figure 1:
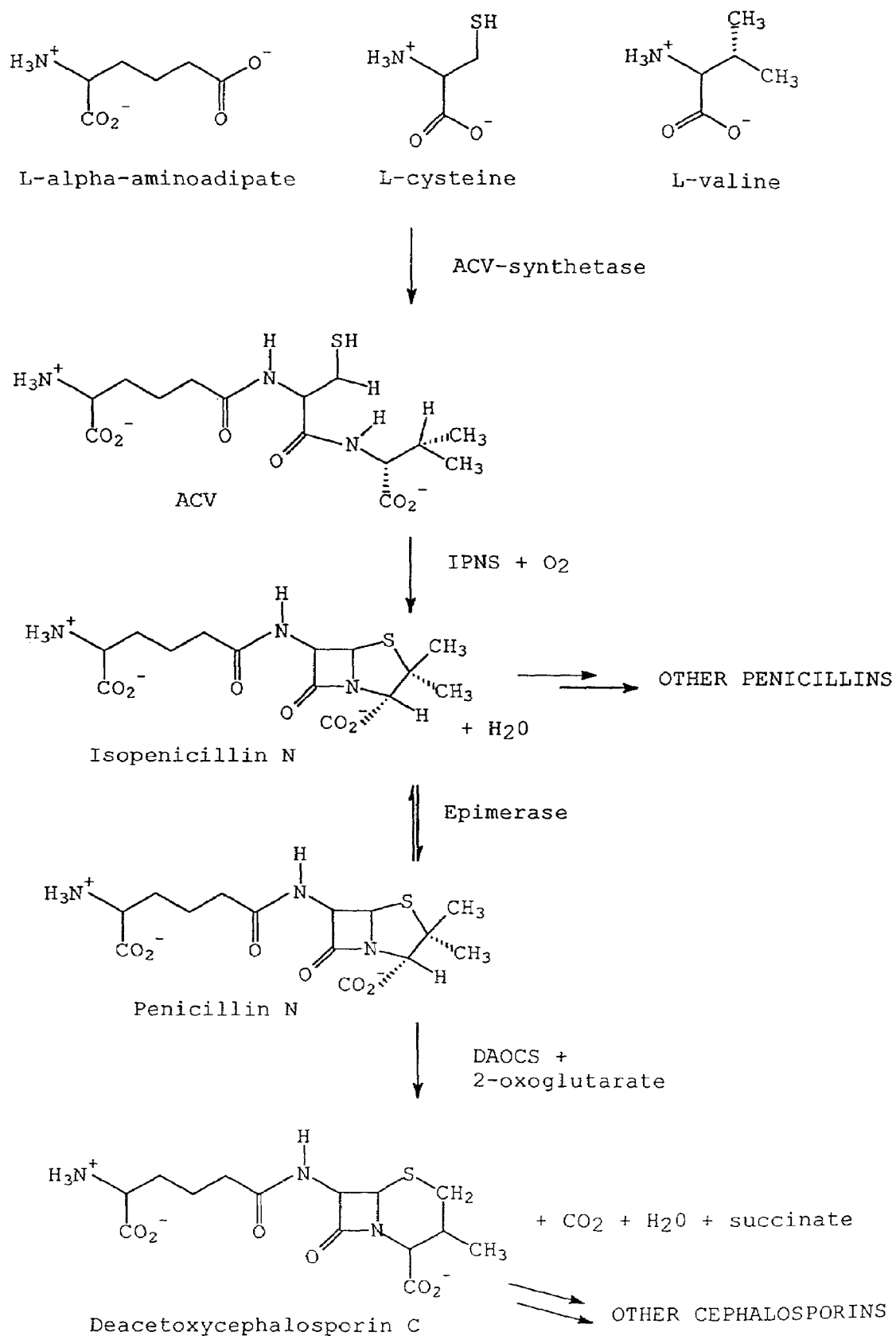
FIG. 1 shows the key steps in the biosynthesis of penicillins and cephalosporins.

The present invention provides a modified isopenicillin N synthetase (IPNS), a modified deacetoxycephalosporin C synthetase (DAOCS), and a modified bifunctional enzyme, deacetoxycephalosporin C synthetase/deacetylcephalosporin C synthetase (DAOCS/DACS). These modified enzymes comprise a mutation that renders the foregoing enzymes regulatable by bicarbonate. Therefore, these modified enzymes allow the production of penicillin or cephalosporin C to be dependent on the presence of bicarbonate. Thus, when modified organisms are provided containing DNA comprising a gene encoding a modified IPNS and/or DAOCS or DACS, the modified organism will express the modified IPNS and/or DAOCS or DAOCS/DACS; however, the modified enzyme will remain inactive until bicarbonate is supplied to activate the enzyme. The term modified when referring to gene or the protein is intended to encompass the term "mutation." The term "modified organism" is intended to encompass organisms that have been modified by genetic engineering or by other methods for generating modified genes in organisms such as chemical mutagenesis or selective cross-overs.

Normally, in the production of an antibiotic by an antibiotic producing organism in a culture, the enzymes involved in the pathway for the production of the antibiotic are continuously produced. However, various enzymes in the pathway are subject to feedback inhibition, which as the amount of antibiotic accumulates, the rate and amount of antibiotic produced decreases. These enzymes, e.g., IPNS, DAOCS, and DAOCS/DACS, have very short half-life because they are particularly susceptible to catalytic and/or non-catalytic inactivation during the enzyme reaction. For example, IPNS, in the presence of its substrate and $O_2$, $Fe^{2+}$ and ascorbate is active for approximately 200 catalytic events before inactivation (Perry et al., Biochem. J. 255: 345–351 (1988)). Therefore, there is a limit as to how much antibiotic can be produced by an antibiotic producing organism in a given culture. The advantage of the present invention is that growing the modified organism expressing the modified enzyme that is bicarbonate-dependent in medium not supplemented with bicarbonate allows the modified organism to be grown to very high levels before bicarbonate is added to the medium to induce antibiotic production.

Therefore, the yield of antibiotic from a culture of modified organisms expressing the bicarbonate-dependent enzyme can be higher than the yield that can be achieved with organisms expressing the native enzyme. The present invention can further allow the use of these modified bicarbonate-dependent enzymes in a cell-free system wherein the enzymes are immobilized on a matrix. Production of antibiotic in the cell free system is regulated by the presence or absence of bicarbonate.

Isopenicillin N synthetase (IPNS), deacetoxycephalosporin C synthetase (DAOCS), and the bifunctional enzyme, deacetoxycephalosporin C synthetase/deacetylcephalosporin C synthetase (DAOCS/DACS), are all members of the same protein structural family; the non-heme Fe(II) dependent family of oxygenases and oxidases, which also includes 1-aminocyclopropane-carboxylic acid (ACC) oxidase. IPNS, DAOCS, and DAOCS/DACS are important in the production of penam and cepham based antibiotics, and ACC oxidase catalyzes the conversion of 1-aminocyclopropane-1-carboxylic acid (ACC) to ethylene, a plant hormone of great significance to agriculture. ACC oxidase, IPNS, DAOCS, and DAOCS/DACS all require ascorbic acid as a co-substrate for activity. Even though these enzymes are from the same family, there are several functional differences between these enzymes. For example, ACC oxidase requires carbon dioxide or bicarbonate as an activator; whereas, IPNS, DAOCS, and DAOCS/DACS do not. Also, DAOCS and DAOCS/DACS require 2-oxo-gluterate as a cofactor in the reaction whereas IPNS and ACC oxidase do not. However, despite these differences, sequence comparisons of ACC oxidases with IPNS and other members of the family of 2-oxoglutarate Fe(II) dependent dioxygenases have shown that an aspartate and two histidine residues are completely conserved throughout this subfamily of Fe(II) dependent oxygenases/oxidases. Further, two completely conserved histidine and aspartate residues in ACC were shown to act as Fe(II) ligands (Zhang et al. Biochem. 36: 15999–16007 (1997); Kadyrzhanova et al. in *Biology and Biotechnology of the Plant Hormone Ethylene*, (1997) Kanellis et al. (eds.), Kluwer Academic Publishers, Netherlands, pp. 5–13). These two histidine residues and the aspartic acid residue is an example of the 2-histidine-1-aspartic acid trifacial motif (Hegg and Que, Eur. J. Biochem. 250: 625–629 (1997)).

There are seven Arg residues that are conserved among the 38 known ACC oxidases. Of these seven, only three are in positions likely to affect enzyme activity. These are Arg244, Arg299, and Arg175. Arg244 in concert with Serine (Ser) at position 246 (Ser246) forms one of the binding sites for the ACC wherein the Ser246 hydrogen bonds to the ACC carboxyl group. The equivalent residues in the *Aspergillus nidulans* IPNS are Arg279 and Ser281 which bind the D-valinyl carboxyl group of δ-(L-α-aminoadipyl)-L-cysteinyl-D-valine (ACV). Since ACC is recognized by ACC oxidase as a D-amino acid, this further shows the similarity of the mechanisms used by ACC oxidase and IPNS in binding their respective substrates. Showing that Arg175 is the essential Arg residue in ACC oxidase was done by covalently modifying Arg residues with 1,2-cyclohexanedione (CHD) and demonstrating that the covalently attached CHD caused almost a complete loss of ACC oxidase activity when CHD was covalently attached to Arg175. Microsequencing of CHD-modified ACC oxidases will confirm that for the inactivated CHD-modified ACC oxidase, Arg175 carries the CHD adduct.

It had been widely accepted that $CO_2$ was the activator for ACC oxidase activity; however, the inventors have determined that ACC oxidase activity is activated by bicarbonate ($HCO_3^-$) and not the gas $CO_2$. In the active site of ACC, the bicarbonate becomes a ligand that is hydrogen or electrostatically bonded to the guanido group of an arginine (Arg) at position 175 (Arg175) such that one oxygen and the $^-OH$ group of bicarbonate is associated with the guanido group and the other oxygen ($O^-$) is placed in close proximity to the catalytic iron atom and to its substrate ACC which is in the reaction center of the enzyme. The oxygen atom ($O^-$) serves as the base catalyst to abstract protons from the ACC amino group in the oxidation of ACC to ethylene. The Arg175 in ACC oxidase is two amino acids upstream of the His residue (His177) which is the iron ligand for the enzyme.

Modified ACC oxidases have been made that have the Arg175 of the oxidase replaced by glutamate (Glu), glutamine (Gln), lysine (Lys), glycine (Gly) or histidine (His). Another modified ACC oxidase Arg175 to alanine (Ala) is being made. It is believed that the Arg175 to Ala and the Arg175 to Gly modified ACC oxidases will be inactive or will require 2-oxo-acids for activity as is true for DAOCS and DAOCS/DACS which have an Ala and Gly residue, respectively, in the equivalent position. However, when the inventors modified the ACC oxidase Arg175 to Glu, Gln, or His by site directed mutagenesis, the Km for bicarbonate in the reaction was increased by about 40-fold and the Vmax for the reaction was reduced by approximately 96%. Glu is not capable of hydrogen bonding to bicarbonate. Both the Gln and His are capable of hydrogen bonding bicarbonate; however, they did not bind as effectively as the Arg175, and bicarbonate activation was not saturable. When the ACC oxidase Arg175 was modified to lysine (Lys), the modified ACC oxidase was about 25% as active as the native ACC oxidase, and bicarbonate activation was saturable. The Lys epsilon amino group is known to bond well to or interact with $CO_2$ or bicarbonate. It is suspected that the reason for the decreased effectiveness is that the placement of the bicarbonate near the iron center by either the Gln residue's amide-bicarbonate adduct or the His residue's imidazole-bicarbonate adduct may not be as favorable as the Arg's guanido-bicarbonate adduct. In contrast, substituting Glu for Arg175 produced an ACC oxidase that was not able to catalyze the reaction. The low non-saturable activation of the Arg175 to Glu modified ACC oxidase can be explained by non-enzyme bound bicarbonate interacting directly with the Fe(II)ACO-ACC-$O_2$ ternary complex.

Finally, computer simulation models indicate that Arg175 of ACC oxidase may rotate within 8 angstroms (Å) of the catalytic iron atom. This modeling was done by mutating the *Aspergillus nidulans* IPNS Glu212 to Arg212 by employing the X-ray coordinates of the IPNS. However, definitive proof that Arg175 in ACC oxidase is within 8 Å of the catalytic iron atom must await until the structure of ACC oxidase has been determined by X-ray crystallography. However, secondary structure analysis by multiple sequence alignment indicates that Arg175 of ACC oxidase is positioned like the Glu212 of IPNS or the Ala181 in DAOCS suggest that the computer simulation model of ACC oxidase is correct.

The foregoing concerning ACC oxidase is relevant to the present invention because it provides a foundation for the present invention which is providing modified IPNS, DAOCS, and DAOCS/DACS with enzymatic activity that is inducible by bicarbonate. In particular, the experiments with ACC oxidase showed that if the amino residue two residues upstream of the His that is an iron ligand in the IPNS, DAOCS, or DAOCS/DACS is modified to an Arg residue, the activity of the enzyme is controllable merely by regulating the level of bicarbonate in cultures of organisms containing the modified IPNS, DAOCS, or DAOCS/DACS.

In the IPNS from *Aspergillus nidulans* (also known as *Emericella nidulans*), the important residue is the Glu at position 212 (Glu212) which is two amino acid residues upstream of the His at position 214 (His214) which is the iron ligand of the enzyme. Glu212 is in a position that is equivalent to the position of Arg175 in ACC oxidase. His214, like His177 in ACC oxidase, is one of the two essential His residues necessary as a ligand to bind the iron cofactor. All other IPNS-producing organisms have a similarly placed Glu residue two residues upstream from the His residue which is an iron ligand of the enzyme. The position number for the Glu and His residues in IPNS from a particular organism varies because of differences in the number of amino acid residues of the IPNS among organisms that produce isopenicillin N. However, the relative position of these two residues correspond in every IPNS regardless of the number of amino acid in the IPNS. The corresponding residues in DAOCS are an Ala residue at position 181 (Ala181) and a His residue at position 183 (His183), and in DAOCS/DACS the corresponding residues are a Gly at position 181 (Gly181) and a His residue at position 183 (His183) or as otherwise numbered in relation to the His214 of IPNS.

None of the important antibiotic-producing organisms has an IPNS, DAOCS, or DAOCS/DACS having an amino acid residue in the position that is two residues upstream from a His, which is generally His214 in IPNS and His183 in DAOCS or DAOCS/DACS, that is capable of bonding with bicarbonate. However, as shown herein, providing a modified IPNS and/or DAOCS or DAOCS/DACS wherein the amino acid residue two residues upstream from the above His residue is changed from the native residue to an Arg residue, the IPNS, DAOCS, or DAOCS/DACS so modified becomes dependent on bicarbonate for activity. Therefore, the present invention provides genetically engineered organisms that express a modified IPNS and/or DAOCS or DAOCS/DACS wherein the mutation is in the gene encoding the IPNS and/or DAOCS or DAOCS/DACS and comprises an Arg codon that is two codons upstream of a His codon that encodes the His that is an iron ligand of the enzyme. Thus, in cultures such as the fermentation cultures used for the production of an antibiotic on a commercial scale that contains any one of these genetically engineered organisms, the production of the antibiotic is bicarbonate dependent. Thus, the activity of the modified enzyme is turned off until bicarbonate is added to the culture. Since the modified enzyme is not subject to feedback inhibition caused by the enzyme's product or a product further downstream in the biosynthesis pathway and catalysis during the enzyme reaction, the maximum amount of organisms and substrate can be produced before the enzyme is turned on by the addition of bicarbonate to the medium. Therefore, the present invention provides a method for making isopenicillin N biosynthesis (and thereby penicillin G or V) by IPNS or cephalosporin C biosynthesis by DAOCS or DAOCS/DACS dependent bicarbonate.

While the Arg modification enables IPNS, DAOCS, or DAOCS/DACS activity to be regulated by bicarbonate, the invention also embraces other amino acids which render the activity bicarbonate dependent. Thus, modifying the amino acid two codons upstream of the His which is an iron binding ligand of the enzyme to Lys can render the enzyme bicarbonate dependent. In certain cases, the modification may affect the enzyme's activity. For example, a modified IPNS comprising a Lys212 or a modified DAOCS or DAOCS/DACS comprising a Lys181 can have an activity that is reduced compared to the modified enzyme having Arg, similar to the 75% reduction in the modified ACC oxidase containing Lys175.

As can been seen, the advantage of the present invention over the prior art is as follows. The organism is grown in culture in log phase in medium not supplemented with bicarbonate using any of the fermentation methods well known in the art. During growth of the organism in culture, the organism accumulates the modified enzyme and the substrate for one of the modified enzyme, e.g., ACV in the case for IPNS and penicillin N in the case for DAOCS or DAOCS/DACS. Thus, an organism comprising the above modified IPNS, ACV accumulates in the organism, and in the case of an organism comprising the above modified DAOCS or DAOCS/DACS (and native IPNS), isopenicillin and its epimer penicillin N accumulate in the organism. When the organism, modified enzyme, and substrate have reached a desired high level, bicarbonate is added to the medium which activates the modified enzyme. Since the enzyme has not participated in the biosynthetic pathway, it has not been subject to catalysis. The activated modified enzyme then converts the accumulated substrate to the desired compound, isopenicillin N (and then penicillin G or V) in the case of an organism comprising the modified IPNS or cephalosporin C in the case of an organism comprising the modified DAOCS or DAOCS/DACS. When the modified IPNS, DAOCS, or DAOCS/DACS is operably linked to a transcription promoter that is not the same as the promoter that naturally regulates transcription (expression) of the IPNS, DAOCS, or DAOCS/DACS, feedback inhibition that affects transcription is abrogated. Therefore, the modified IPNS, DAOCS, or DAOCS/DACS can accumulate to much higher levels in the organism than could the native enzyme. Thus, increasing the yield of the above antibiotic products when the enzyme is activated by bicarbonate.

In a preferred embodiment, the native gene encoding IPNS, DAOCS, or DAOCS/DACS of the host organism is replaced with a modified IPNS and/or DAOCS or DAOCS/DACS comprising a mutation of the codon two codons upstream of the codon encoding His which is an iron ligand of the enzyme wherein the mutation is a codon encoding Arg to make the modified organism of the present invention. In an alternative embodiment of the present invention, the mutation is where the codon encodes Lys instead of Arg. Methods for making modified organisms such as fungi wherein the native gene is replaced by a modified gene are well known in the art. For example, Campbell et al. in Curr. Genet. 16: 53–56 (1989) teach transformation of *Aspergillus niger* and show that most integration events are as a result of homologous integration; Bird and Bradshaw in Mol. Gen. Genet. 255: 219–225 (1997) teach transformation and gene targeting in *Aspergillus nidulans*; and, Sanchez et al. in Mol. Gen Genet. 258: 89–94 (1998) teaches an improved method for transforming *Aspergillus nidulans* via restriction enzyme-mediated integration. These modified organisms are useful when it is desirable to have all antibiotic biosynthesis dependent on bicarbonate which enables antibiotic production to be turned on or off at a particular times during culture.

Alternatively, modified organisms that have mutations that encode inactive forms of IPNS, DAOCS, or DAOCS/DACS can be used to make the organisms of the present invention. For example *Acremonium chrysogenum* strain N2 has a mutation in the IPNS gene and hence does not produce cephalosporin C (disclosed in U.S. Pat. No. 5,462,862 to Groenen et al.). Therefore, transforming strain N2 with the modified gene encoding the bicarbonate dependent IPNS produces an organism that produces cephalosporin C only when the culture is supplemented with bicarbonate.

While it is preferable that the modified organism comprising the modified IPNS and/or DAOCS or DAOCS/DACS does not contain the native IPNS and/or DAOCS or DAOCS/DACS activity, in another embodiment of the invention the modified organism comprises both the native enzyme and the modified enzyme operably linked to a different promoter. Thus, even though the native IPNS in the organism is active during most of the culturing process, the accumulated downstream products will eventually turn off expression of the native IPNS and catalysis will destroy the remaining native IPNS. Meanwhile, expression of the modified IPNS has continued during the entire growth phase of the organism resulting in the accumulation of a large quantity of the modified IPNS in the organism. Thus, production of the antibiotic will resume when bicarbonate is added to the culture because the accumulated modified IPNS was destroyed by catalysis since it was inactive and its expression had not been turned off because it is not operably linked to the native IPNS promoter.

It is to be appreciated that production of any antibiotic such as penams or cephams that is dependent on ACV synthetase and IPNS to make isopenicillin N which is precursor for the downstream antibiotic can be made bicarbonate dependent by providing a modified gene encoding bicarbonate-dependent IPNS to organisms that produces the antibiotic. For example, organisms that make cephams such as *Cephalosporium, Spiroidium, Scopulariopsis, Diheterospora, Peacilomyces, Streptomyces, Nocardia, Flavobacterium, Xanthomas*, and *Lysobacter*; organisms such as *Streptomyces* that can also make clavams; organisms that make carbapenems such as *Streptomyces, Serratia*, and *Erwinia*; and, organisms that make monobactams such as *Nocardis, Pseudomonas, Gluconobacter, Chromobacterium, Agrobacterium*, and *Acetobacter*. In all of these organisms, the antibiotic produced is made bicarbonate dependent by modifying the organism to comprise a gene encoding an IPNS that is modified to have an Arg codon that is two codons upstream of a His codon that encodes a His that is an iron ligand of the IPNS. Thus, production of the antibiotic is bicarbonate dependent since in the absence of the bicarbonate, the inactive IPNS does not produce the isopenicillin N which is the precursor for the downstream antibiotic. When bicarbonate is supplied to the organism, the IPNS is activated and cyclizes ACV to isopenicillin N which then serve as a substrate for the downstream antibiotic, whether it be a cepham, clavam, carbapenem, or monobactam.

In another embodiment of the present invention, modified genes encoding modified IPNS, DAOCS, or DAOCS can be used to transform host strains that do not possess the native gene counterpart to the modified gene. For example, *Penicillium* and *Aspergillus* do not possess the genes encoding enzymes for the cephalosporin and cephamycin pathways, whereas *Cephalosporium* and *Streptomyces* possess these genes. Therefore, introducing modified genes encoding bicarbonate-dependent DAOCS or DAOCS/DACS into *Penicillium* or *Aspergillus* which makes penicillin but not cephalosporin and cephamycin will result in biosynthesis of cephalosporin or cephamycin by the modified *Penicillium* or *Aspergillus* when cultivated in the presence of bicarbonate. In a preferred embodiment, the modified *Penicillium* or *Aspergillus* further comprises a modified gene encoding bicarbonate-dependent IPNS. Alternatively, the modified organism comprising a modified IPNS, is further modified to comprise the native forms of DAOCS or DAOCS/DACS. In this modified organism, the production of the cepham is solely dependent on the modified IPNS.

In a preferred embodiment, the modified organism comprising the modified IPNS and/or DAOCS or DAOCS/DACS is a fungus derived from such fungi as *Aspergillus nidulans, Penicillium chrysogenum, Acremonium chrysogenum, Acremonium chrysogenum* (strain M8650), and *Cephalosporium acremonium* or is a bacterium derived from such bacteria as *Streptomyces clavuligerus, Streptomyces cattleya, Streptomyces clavuligerus* (strain NRRL 3585), and *Streptomyces anulatus* (*Streptomyces lipmanii*). In other embodiments, the modified organism comprising a modified gene encoding a modified IPNS and/or DAOCS or DAOCS/DACS dependent on bicarbonate for activity is *E. coli*. When the bacteria is *E. coli*, the bacteria further comprises the gene encoding ACV synthetase. Bacteria comprising the modified gene encoding the modified IPNS and/or DAOCS or DACS/DAOCS are an efficient means for obtaining large amounts of the modified enzyme. A large source of the modified enzyme is useful for cell-free systems for producing an antibiotic. When the modified organism is a bacterium, it is preferable that the modified gene encoding the modified IPNS, DAOCS, or DAOCS/DACS be in a plasmid vector wherein the modified gene produces an abundance of the modified IPNS, DAOCS, or DAOCS/DACS which can then be purified for use in cell-free systems for making antibiotics. In a preferred embodiment, modified IPNS and/or DAOCS or DAOCS/DACS are attached to a support matrix to use in vitro to make isopenicillin N or cephalosporin C, respectively, or other known or novel antibiotic. A cell-free system for producing an antibiotic is particularly useful for making novel antibiotics. For example, IPNS is not only useful for the production of isopenicillin N, but also for the condensation of other tripeptides other than ACV to form novel antibiotics.

Genes encoding IPNS, DAOCS, or DAOCS/DACS, methods for cloning genes involved in antibiotic biosynthesis, recombinant DNA vectors useful for transforming fungi and bacteria, and methods for transforming fungi and bacteria with the recombinant DNA vectors are disclosed in U.S. Pat. No. 4,885,251 to Ingolia et al., U.S. Pat. No. 4,885,252 to Ingolia et al., U.S. Pat. No. 4,892,819 to Carr et al., U.S. Pat. No. 4,950,603 to Ingolia et al., U.S. Pat. No. 5,070,020 to Ingolia et al., U.S. Pat. No. 5,462,862 to Goenen et al., U.S. Pat. No. 5,753,435 to Aharonowitz et al., U.S. Pat. No. 5,882,879 to Veenstra et al., U.S. Pat. No. 5,882,883 to Egel-Mitani et al., and U.S. Pat. No. 5,942,411 to Kaasgaard et al., which are all hereby incorporated herein by reference. The above incorporated U.S. patents disclose DNAs containing genes that encode various IPNS, DAOCS, and DAOCS/DACS, recombinant DNA vectors containing these genes, and methods for transforming various strains of fungi and bacteria with recombinant DNA vectors which are useful for practicing the present invention. The genes taught in the above incorporated U.S. patents can be modified as taught by the present invention to make the modified IPNS, DAOCS, and DAOCS/DACS of the present invention wherein the codon that is two codons upstream of the codon encoding a His which is an iron ligand for the encoded enzyme is changed to a codon encoding Arg. The transformation protocols disclosed in the above incorporated U.S. patents are followed to make the modified organisms of the present invention which express the modified IPNS and/or DAOCS or DAOCS/DACS which is dependent on bicarbonate for activity.

It will be appreciated by one skilled in the art, that the gene encoding the modified IPNS, DAOCS, or DAOCS/

DACS in the plasmid vector can contain its own native promoter sequence which is recognized by an RNA polymerase of the host cell, or the modified IPNS, DAOCS, or DAOCS/DACS can be operably linked to any other suitable promoter, e.g., that of a different β-lactam biosynthetic gene, or that of a glycolytic gene such as phosphoglycerate kinase, glyceraldehyde phosphate dehydrogenase, triose phosphate isomerase, or that of the translational elongation factor, Ef-Tu, or the like. In addition, each cloned modified gene will have a transcription termination sequence operably linked to the 3' end of the gene. Examples of promoter and termination sequences that are useful for controlling transcription of the modified IPNS, DAOCS, and DAOCS/DACS in vivo or in vitro are disclosed in the above incorporated U.S. Patents.

The modified genes of the present invention encoding IPNS, DAOCS, or DAOCS/DACS are preferably made using site directed mutagenesis. Methods for site directed mutagenesis are well known in the art and kits comprising these methods are commercially available. For example, detailed methods for site directed mutagenesis can be found in Sambrook et al. (Eds.), *Molecular Cloning: A Laboratory Manual, Second Edition*, Cold Spring Harbor Laboratory Press, Cold Spring Harbor, N.Y. (1989) and kits are available from Stratagene, Clonetech, and others. As an example, the Glu212 to Arg conversion of *Aspergillus nidulans* is made by performing site directed mutagenesis on an IPNS cDNA which is subcloned into a pET-15b plasmid vector that overexpress the IPNS in *E. coli* strain BL21(DE)pLysS cells as a His-Tag fusion protein. The His-Tag facilitates purification of the modified IPNS by metal column chromatography. This method has been used by the inventors to prepare more than 50 site-directed modified genes encoding ACC oxidase. IPNS activity for the modified and a non-modified IPNS cloned in the same manner as the modified IPNS is determined using established bioassay protocols performed with and without bicarbonate. The Glu212 to Arg conversion is dependant on bicarbonate for activity because it produces isopenicillin N in the presence of bicarbonate but not in the absence of bicarbonate. *Aspergillus nidulans* strains b1A1, FGSC-4, and bioA1 all have in the gene encoding IPNS the codon encoding Glu at position 212. While the Glu to Arg mutation is described herein, similar mutations in the IPNS from other organisms can be made in the manner described herein for *Aspergillus nidulans*.

Alternatively, the above modified IPNS, DAOCS, or DAOCS/DACS encoding sequences, promoter sequences, and transcription termination sequences is synthesized by the modified phosphotriester method using fully protected deoxynucleotides. These DNA synthesis methods are well known in the art. A manual DNA synthesis method is disclosed in Hsiung et al., Nuc. Acid Res. 11: 3227 (1983) and Narang et al., Methods in Enzymology 68: 70 (1980). In a preferred method, the DNA sequence is synthesized using automated DNA synthesizers such as Systec 1450A or ABS 380A DNA synthesizers. The advantage of chemically synthesizing the modified gene is that any restriction enzyme site can be introduced into or removed from the sequence comprising the synthetic gene which facilitates the subsequent steps of cloning the modified gene.

The following are examples of where the Arg modification is made in other genes encoding IPNS from other organisms. A bicarbonate-dependent IPNS of *Penicillium chrysogenum* is made by modifying the codon encoding Glu at position 212 (Glu212) in the gene encoding the IPNS to an Arg codon (Arg212). A bicarbonate-dependent IPNS of *Streptomyces clavuligerus* is made by modifying the codon encoding Glu at position 210 (Glu210) in the gene encoding the IPNS to an Arg codon (Arg210). A bicarbonate-dependent IPNS of *Acremonium chrysogenum* is made by modifying the codon encoding Glu at position 214 (Glu214) in the gene encoding the IPNS to an Arg codon (Arg214). A bicarbonate-dependent IPNS of *Acremonium chrysogenum* (strain M8650) is made by modifying the codon encoding Glu at position 214 (Glu214) in the gene encoding the IPNS to an Arg codon (Arg214). A bicarbonate-dependent IPNS of *Streptomyces cattleya* is made by modifying the codon encoding Glu at position 211 (Glu211) in the gene encoding the IPNS to an Arg codon (Arg211). A bicarbonate-dependent IPNS of *Streptomyces clavuligerus* (strain NRRL 3585) is made by modifying the codon encoding Glu at position 211 (Glu211) in the gene encoding the IPNS to an Arg codon (Arg211). A bicarbonate-dependent IPNS of *Streptomyces anulatus* (*Streptomyces lipmanii*) is made by modifying the codon encoding Glu at position 214 (Glu214) in the gene encoding the IPNS to an Arg codon (Arg214). A bicarbonate-dependent DAOCS of *Streptomyces clavuligerus* is made by modifying the codon encoding Ala at position 181 in the gene encoding the DAOCS to an Arg codon (Arg181) as shown in SEQ ID NO:18. The DNA sequence encoding the native DAOCS is available from Genbank as accession no. M32324 M24140. While the above mentioned refer to Arg modifications, the present invention also embraces other modifications which render the enzyme bicarbonate dependent, such as modifying the codon to Lys.

There are six different codons that encode Arg. These codons are CGA, CGC, CGG, CGU, AGA, and AGG. When site directed mutagenesis is performed on a cloned DNA molecule comprising a gene encoding IPNS, DAOCS, or DAOCS/DACS, the codon modified to encode Arg can be any one of the six above codons. Therefore, the present invention provides a modified gene encoding IPNS, DAOCS, or DAOCS/DACS wherein any one of codons CGA, CGC, CGG, CGU, AGA, or AGG can replace the codon that is in the position that is two codons upstream from the codon encoding a His which is an iron ligand in the enzyme. Two codons encode Lys, AAA and AAG. Therefore, present invention also provides a modified gene encoding IPNS, DAOCS, or DAOCS/DACS wherein either codon AAA or AAG can replace the codon that is in the position that is two codons upstream from the codon encoding a His which is an iron ligand in the enzyme.

FIG. 2 shows the amino acid sequence flanking the histidine residue that is the iron ligand of IPNS. The amino acid sequence for IPNS is highly conserved between fungi and bacteria. Thus, SEQ ID Nos. 1 to 10 show the expected amino acid sequences for modified IPNS from a variety of fungi and bacteria which are made according to the present invention wherein the modification comprises an Arg residue that is two amino acid residues upstream of the His residue, which is an iron ligand in the IPNS. For all of these examples, the corresponding amino acid residue in the native IPNS that is two amino acid residues upstream of the His residue which is an iron ligand of the enzyme, is a Glu residue. SEQ ID NO:1 shows the amino acid sequence of a modified IPNS of *Emericella nidulans* (*Aspergillus nidulans*) strain b1A1 showing an Arg212 in place of Glu212. The DNA from strain b1A1 encoding the native IPNS is available as Genbank accession no. M18111. SEQ ID NO:2 shows the amino acid sequence of a modified IPNS of *Emericella nidulans* (*Aspergillus nidulans*) strain FGSC-4 showing an Arg212 in place of Glu212. The DNA from strain FGSC-4 encoding the native IPNS is available as Genbank accession no. M21882. SEQ ID NO:3 shows the amino acid sequence of a modified IPNS of *Emericella nidulans* (*Aspergillus nidulans*) strain bioA1 showing an Arg212 in place of Glu212. The DNA from strain bioA1 encoding the native IPNS is available as Genbank accession no. A10846. SEQ ID NO:4 shows the amino acid sequence of a modified IPNS of *Penicillium chrysogenum* showing an Arg212 in place of Glu212. The DNA from *P. chrysogenum* encoding the native IPNS is available as Genbank accession no. M15083. SEQ ID NO:5 shows the amino acid sequence of a modified IPNS of *Streptomyces clavuligerus* showing an Arg210 in place of Glu210. The DNA from *S. clavuligerus* encoding the native IPNS is available from Genbank as accession no. A01132. SEQ ID NO:6 shows the amino acid sequence of a modified IPNS of *Acremonium chrysogenum* showing an Arg214 in place of Glu214. The DNA from *A. chrysogenum* encoding the native IPNS is available from Genbank as accession no. E01000. SEQ ID NO:7 shows the amino acid sequence of a modified IPNS of *Acremonium chrysogenum* strain M8650 showing an Arg214 in place of Glu214. The DNA from strain M8650 encoding the native IPNS is available as Genbank accession no. M33522. SEQ ID NO:8 shows the amino acid sequence of a modified IPNS of *Streptomyces cattleya* showing an Arg211 in place of Glu211. The DNA from *S. cattleya* encoding the native IPNS is available as Genbank accession no. D78166. SEQ ID NO:9 shows the amino acid sequence of a modified IPNS of *Streptomyces clavuligerus* strain NRRL 3585 showing an Arg210 in place of Glu210. The DNA from strain NRRL 3585 encoding native IPNS is available from Genbank as accession no. M19421. SEQ ID NO:10 shows the amino acid sequence of a modified IPNS of *Streptomyces anulatus* showing an Arg214 in place of Glu214. The DNA from *S. anulatus* encoding the native IPNS is available from Genbank as accession no. M22081. While the above mentioned sequences show Arg in the position two amino acid residues upstream from the His residue that is an iron ligand of the enzyme, the same position can also be a Lys. The sequences from above mentioned Genbank accession numbers are hereby incorporated herein by reference.

In a preferred embodiment, the present invention provides a genetically engineered *Aspergillus nidulans* that overproduces an IPNS containing the Glu212 to Arg mutation. Alternatively, the mutation may be a Glu212 to Lys mutation. A control *Aspergillus nidulans* contains the native IPNS. The Glu212 to Arg modified IPNS of *Aspergillus nidulans* produces an IPNS that is bicarbonate-dependent because it produces isopenicillin N only when the media is supplemented with bicarbonate. The relative production rates of the modified IPNS and the native IPNS is compared by cyclically raising and lowering the bicarbonate under dialysis to remove the isopenicillin N product to prevent feedback inhibition. The modified strain is a superior producer of isopenicillin N because the total isopenicillin N produced by the modified strain is higher than the native strain.

Other genetically engineered or modified organisms for producing IPNS include: a genetically engineered *Penicillium chrysogenum* wherein the codon encoding Glu at position 212 (Glu212) in the gene encoding the IPNS is modified to encode Arg (Arg212); a genetically engineered *Streptomyces clavuligerus* wherein the codon encoding Glu at position 210 (Glu210) in the gene encoding the IPNS is modified to encode Arg (Arg210); a genetically engineered *Acremonium chrysogenum* wherein the codon encoding Glu at position 214 (Glu214) in the gene encoding the IPNS is modified to encode Arg (Arg214); a genetically engineered *Acremonium chrysogenum* (strain M8650) wherein the codon encoding Glu at position 214 (Glu214) in the gene encoding the IPNS is modified to encode Arg (Arg214); a genetically engineered *Streptomyces cattleya* wherein the codon encoding Glu at position 211 (Glu211) in the gene encoding the IPNS is modified to encode Arg (Arg211); a genetically engineered *Streptomyces clavuligerus* (strain NRRL 3585) wherein the codon encoding Glu at position 211 (Glu211) in the gene encoding the IPNS is modified to encode Arg (Arg211); and a genetically engineered *Streptomyces anulatus* (*Streptomyces lipmanii*) wherein the codon encoding Glu at position (Glu214) in the gene encoding the IPNS is modified to encode Arg (Arg214). The above mentioned modifications can also be a Lys instead of the Arg.

While the present invention describes Glu to Arg or Lys mutations in the IPNS of *Aspergillus nidulans, Penicillium chrysogenum, Streptomyces clavuligerus, Acremonium chrysogenum, Acremonium chrysogenum* (strain M8650), *Streptomyces cattleya, Streptomyces clavuligerus* (strain NRRL 3585), and *Streptomyces anulatus* (*Streptomyces lipmanii*), the present invention is not to be construed as limited to these organisms or to IPNS. The present invention includes other enzymes that are members of the non-heme iron (II) dependent family of oxygenases and oxidases from any organism. Examples of organisms that have enzymes that are members of the non-heme iron (II) dependent family of oxygenases and oxidase that are encompassed by the present invention: *Cephalosporium acremonium* (produces penicillins and cephalosporins), *Penicillium chrysogenum* (produces various penicillins and other β-lactams), *Acremonium chrysogenum* (produces various penicillins), *Emericella nidulans* (produces various penicillins), *Nocardia lactamdurans* (produces cephamycin C), *Nocardia uniformus* (produces nocardicin), *Streptomyces antibioticus* (produces clavulanic acid), *Streptomyces anulatus* (produces penicillins), *Streptomyces argenteolus, Streptomyces cattleya* (produces thienamycin), *Streptomyces chartreusis* (produces SF 1623 and cephamycin A and B), *Streptomyces clavuligerus* (produces PA-32413-I, cephamycin C, A16886A, penicillins, cephalosporins, clavulanic acid, and other clavams), *Streptomyces fimbriatus* (produces cephamycin A and B), *Streptomyces flavovirens* (produces MM 4550 and MM 13902), *Streptomyces flavus* (produces MM 4550 and MM 13902), *Streptomyces fulvoviridis* (produces MM 4550 and MM 13902), *Streptomyces griseus* (produces cephamycin A and B, and carpetimycin A and B), *Streptomyces halstedi* (produces cephamycin A and B), *Streptomyces heteromorphus* (produces C2081X and cephamycin A and B), *Streptomyces hygroscopicus* (produces deacetoxycephalosporin C), *Streptomyces lactamdurans* (produces penicillins), *Streptomyces lipmanii* (produces cephamycin, penicillin N, 7-methoxycephalosporin C, A16884, MM4550, and MM13902), *Streptomyces olivaceus* (produces epithienamycin F, MM 4550, and MM 13902), *Streptomyces panayensis* (produces C2081X and cephamycin A and B), *Streptomyces pluracidomyceticus* (produces pluracidomycin A), *Streptomyces rochei* (produces cephamycin A and B), *Streptomyces sioyaensis* (produces MM 4550 and MM 13902), *Streptomyces* sp. OA-6129 (produces OA-6129A), *Streptomyces* sp. KC-6643 (produces carpetimycin A), *Streptomyces tokunomensis* (produces asparenomycin A), *Streptomyces viridochromogenes* (produces cephamycin A and B), *Streptomyces wadayamensis* (produces WS-3442-D), *Agrobacterium* (produces various β-lactams), *Gluconobacter* (produces various β-lactams), *Serratia* (produces various β-lactams), and Actinomycetes and other filamentous fungi.

This list is merely to serve as an example of the various antibiotic producing organisms encompassed by the present invention; therefore, the present invention is not to be construed as limited to the organisms enumerated herein.

The present invention further includes any of the antibiotic producing enzymes of the non-heme Fe II family wherein the enzyme is further modified by other mutations that increase stability of the enzyme, increase the enzyme's reaction rate, or modify the substrate specificity of the enzyme. Therefore, the present invention includes any mutation in the non-heme iron (II) dependent enzyme wherein the amino acid residue two residues upstream of the His residue which is an iron ligand of the enzyme is modified to an amino acid residue that is able to hydrogen bond or electrostatically bond bicarbonate at that site and participate in the enzymatic reaction. For example, U.S. Pat. No. 5,919,680 to Sutherland which is hereby incorporated herein by reference discloses a genetically engineered Penicillin chrysogenum comprising a DAOCS of Streptomyces clavuligerus with altered substrate specificity. The native DAOCS has substrate specificity for isopenicillin N whereas the altered enzyme has specificity for penicillin G. Therefore, the altered enzyme can be used to produce novel antibiotics. The altered DAOCS can be modified according to the present invention to comprise an Arg residue two residues upstream of the His which is an iron ligand of the enzyme wherein the activity of the altered enzyme is bicarbonate dependant. The modified altered enzyme that is bicarbonate dependant can be used according to the method of the present invention to produce novel antibiotics. The incorporated reference demonstrates to those skilled in the art that any of the non-heme II family of enzymes can be modified or modified to altered substrate specificity. Therefore, the present invention includes any of these enzymes wherein the enzyme's substrate specificity has been altered.

The modified organisms of the present invention can be used in a method to produce the appropriate antibiotic using fermentation culture technology which is well known in the art. In the method, the media used to grow the modified organisms does not contain supplemental bicarbonate. Also in the method, the modified organism is grown to a level that is less than saturation for the modified organism. Thus, the modified organism accumulates the substrate for the enzyme that was modified. When predetermined growth parameters of the modified organism have been reached which is known to produce the maximal amount of the antibiotic, bicarbonate is added to the media. The bicarbonate enables the modified enzyme to produce the antibiotic. The antibiotic is then harvested from the media. As an alternative to adding bicarbonate to the media, gaseous $CO_2$ can be added to the media. To maintain bicarbonate at a naturally low level in the media prior to addition of the bicarbonate or $CO_2$, the organisms are grown under reduced pressure or in medium of low pH.

In one embodiment of the method for producing the antibiotic using fermentation culture technology, the culture, after activation of the modified enzyme, is passed through a counter-current dialysis device which removes the antibiotic from the media. Afterwards, the modified organisms can be returned to media without supplemental bicarbonate and allowed to once again accumulate the substrate for the modified enzyme. To maintain the modified organisms at a level below saturation, sufficient organisms are removed from the fermentation culture. When the modified organisms have again produced the predetermined amount of substrate, bicarbonate is added to the media, and the antibiotic is removed from the media as above. In this manner, a fermentation culture of the modified organism for producing an antibiotic can be maintained for an extended period of time. The fermentation culture can be according to methods well known in the art for batch fermentation or according to methods well known in the art for continuous flow fermentation.

The following examples are intended to promote a further understanding of the present invention.

EXAMPLE 1

This example shows the cloning of a gene encoding IPNS from Aspergillus nidulans. The method is suitable for cloning and expression of IPNS from other organisms. This example is based on the protocol of Wiegel et al., J. Bacteriol. 170: 3817–3826 (1988) for cloning the IPNS gene of A. nidulans.

Spores of A. nidulans are used to inoculate YG (2% glucose, 0.05% yeast extract) broth medium. The inoculated medium is incubated at 37° C. for 48 hours with agitation (250 rpm). Mycelia are harvested by vacuum filtration (Whatman no. 1 filter) and washed with an equivalent volume of sterile water. The washed mycelia are transferred to a mortar containing liquid nitrogen and ground to a powder with a pestle. The powdered mycelia are re-suspended in 2 ml lysis buffer containing 2% sodium dodecyl sulfate (SDS), 0.1 M EDTA, 10 mM Tris-HCl, pH 7.8, and 0.1 mg proteinase K at a final concentration of 0.5 gram of cells per ml. The suspension is incubated at 60° C. for 1 hour. Afterwards, NaCl is added to a final concentration of 1.0 M and the suspension incubated at 4° C. for about 1 hour. Cell debris is then removed from the suspension by centrifugation in a Sorvall RC-5B using a GSA rotor at 6,000 rpm for 20 minutes. Nucleic acids are precipitated from the supernatant fraction with and equal volume of isopropanol and the precipitate collected by centrifugation. The nucleic acid pellet is suspended in TE buffer (10 mM Tris-HCl, pH 7.5, 0.1 mM EDTA) and DNase-free RNASE is added to the suspension to remove the RNA. The remaining protein in the suspension is extracted with phenol and chloroform. The DNA is precipitated in two volumes of ethanol, harvested by spooling, and air-dried. The DNA is re-suspended in TE buffer.

The DNA is used to make a lambda library comprising the A. nidulans genome. The A. nidulans DNA from above is partially digested with Sau3AI to achieve an average fragment size of 10 to 20 kilobases (kb). These fragments are ligated into the BamHI site of a lambda cloning vector using a cloning kit such as the Lambda EMBL3 Vector Kit comprising lambda EMBL-3 or the ZAP EXPRESS vector Kit comprising lambda ZAP Express, both available from Stratagene, La Jolla, Calif. The manufacturer's instructions are used for cloning and purifying the lambda clones.

The library is screened using the C. acremonium IPNS gene encoded on plasmid pIT335, available from the Northern Regional Research Laboratories, Agricultural Research Service, U.S. Department of Agriculture, Peoria, Ill. 61604, under accession No. NRRL B-15960. The pIT335 probe is radiolabeled with $^{32}P$ by nick translation. The labeled probe is used to screen portions of the of the lambda library immobilized on nitrocellulose filters. Hybridizations are carried out in 30% formamide-5×SSC (1×SSC is 0.15 M NaCl and 0.015 M sodium citrate) at 37° C. and then washed in 5×SSC at 65° C. A recombinant lambda is isolated which hybridizes to the radiolabeled pIT335 probe. The above method for cloning genes in lambda vectors is well known in the art. The above method and other methods equivalent in result for cloning an IPNS from *A. nidulans* or other organism can be found in Sambrook et al. (eds.) in *Molecular Cloning: A Laboratory Manual, Second Edition.* Cold Spring Harbor Laboratory Press, Cold Spring Harbor, N.Y. (1989).

EXAMPLE 2

This example shows a method that uses site-specific mutagenesis of the IPNS gene of *Aspergillus nidulans* to convert the codon that is two codons upstream from the codon that encodes a His which is an iron ligand of the enzyme to a codon that encodes Arg.

A site-directed modified *Aspergillus nidulans* is made by using the unique restriction enzyme site elimination method of Deng and Nickoloff, Anal. Biochem. 200: 81–88 (1992) which is commercially available in kit form. A target plasmid clone containing the gene encoding IPNS of *A. nidulans* from Example 1 in the T7 promoter based expression vector pET-15b with a HIS-TAG thrombin site is provided and a mutagenic oligonucleotide primer having the sequence 5'-CTG AGT TTT GAG TGG CAT CGG GAT GTA ATC-3' (SEQ ID NO:17) is provided. The oligonucleotide has the codon CGG which encodes Arg instead of the native codon GAG which encodes Glu. Besides the above primer, the USE method uses a selection primer which mutates a restriction enzyme site unique to the plasmid for purposes of selection. In this example, the oligonucleotide sequence used converts a ScaI site in the pET-15b vector to an MluI site. This primer was designed by Pharmacia Biotech and is available from Pharmacia Biotech. The TRANSFORMER site-directed mutagenesis kit from Clonetech is used according to the manufacturer's instructions. The mutagenic and selection primers are simultaneously annealed to the double-stranded target plasmid. After DNA elongation and ligation, the heteroduplex DNA is used to transform the repair-deficient *E. coli* strain BMH71-18 mutS. Plasmids prepared from the pool of transformants are subjected to selection restriction enzyme digestion to enrich for plasmids that carry the selection primer sequence. After final transformation into *E. coli* strain BL21 (DE3) pLysS, plasmids are isolated from individual colonies and are analyzed for the presence of the selection and mutagenic primer sequence. The Arg mutation is confirmed by DNA sequencing.

While this example uses the IPNS cloned into pET-15b, the method is applicable to the same mutagenesis method wherein a gene encoding DAOCS or DAOCS/DACS is cloned into pET-15b. In the case of mutagenizing DAOCS or DAOCS/DACS, the mutagenesis primers comprise the codon for Arg in lieu of the codon for Ala181 or Gly181, and the flanking sequences of each of the primers correspond to the sequence in DAOCS or DAOCS/DACS, respectively. One skilled in the art will appreciate that the above method can be used for any one of IPNS, DAOCS, or DAOCS/DACS cloned into any plasmid that is convenient for the mutagenesis reaction.

EXAMPLE 3

This example shows the transformation of *Aspergillus nidulans* with DNA encoding the IPNS gene comprising the Glu212 to Arg mutation. The transformed *A. nidulans* produced by this method has the native gene replaced by the modified IPNS gene comprising the Glu212 to Arg mutation.

50 ml of MMC medium in a 250 ml baffled shake flask is inoculated with two plates of spores, grown for 6 days on Le Page-Campbell sporulation medium. Cultures are incubated for 24 to 30 hours at 28° C. with shaking at 200 rpm. Mycelium is collected by filtration through a nylon filter (25 μm pore) and excess water is removed by pressing between filter papers. The isolated mycelium is resuspended at 50 mg/ml in TPC buffer (0.8 M NaCl; 0.02 M $MgSO_4$; 50 mM potassium phosphate buffer, pH 7.0) with 10 mM DTT; the mycelium is incubated with shaking at 28° C. for 90 minutes. Afterwards, the mycelium is collected by centrifugation (5 minutes at 2,500 rpm) and resuspended at about 25 mg/ml in TPC containing NOVOZYM. The suspension is incubated with shaking for 2–5 hours at 28° C. Protoplasts are filtered through a 25 μm pore nylon filter and isolated by centrifugation (5 minutes at 2,000 rpm). The protoplast pellet is washed three times with 0.8 NaCl. Protoplasts are resuspended in 10 ml of NMC buffer (0.8 M NaCl; 50 mM $CaCl_2$; 10 mM MOPS, pH 7.0), then pelleted and re-suspended in 5× the pellet volume of NMC buffer. The final concentration is about $10^8$ protoplasts per ml. Then 0.1 volume of CCM buffer (0.8 M NaCl; 50 mM CaCl2; 10 mM MOPS, pH 7.0) is added. For each transformation, DNA comprising the modified IPNS gene and a reporter gene that confers resistance to pleomycin and 100 μl of the protoplast suspension are mixed and stored on ice for 20 minutes. Then 500 μl of CCM buffer is added to each transformation sample and the mixture is stored at room temperature for another 20 minutes. Then the transformation mixture is diluted with 600 μl of NMC buffer and plated on TSA-sucrose containing 10 μg/ml of pleomycin. Plates are incubated at 28° C. for 2–6 days. Then transformants are inoculated on pleomycin containing plates; after growth, spores are generated on Le Page-Campbell sporulation medium. Transformed fungi comprising the modified IPNS gene that encodes IPNS dependent on bicarbonate for activity are selected using methods well known in the art.

Following the above method, transgenic *Aspergillus nidulans* further comprising a modified gene encoding modified DAOCS or DACS dependent on bicarbonate for activity can be made.

In general, the above embodiments and examples disclose modified organisms containing a modified IPNS, DAOCS, or DAOCS/DACS wherein the modified enzyme is dependent on bicarbonate for activity, the present invention is not to construed as limited thereto. The present invention further provides organisms that comprise a modified IPNS and a modified DAOCS or DAOCS/DACS to make the production of the antibiotic bicarbonate dependent. For example, a modified Cephalosporin or *Streptomyces* can be made which contains both a modified IPNS and a modified DAOCS. It is also to be appreciated that while various fungal and bacterial species have been enumerated which possess an IPNS and/or DAOCS or DAOCS/DACS that can be modified according to the present invention, the present invention further includes all fungal and bacterial species that encode IPNS and/or DAOCS or DAOCS/DACS whether known or yet to be discovered.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An isolated polynucleotide encoding a mutant isopenicillin N synthetase (IPNS) consisting of the amino acid sequence SEQ ID NO:1, wherein said mutant continues to have IPNS activity but is dependent on bicarbonate as an activator in producing penicillin.

2. The isolated polynucleotide of claim 1, wherein the isolated polynucleotide is isolated from *Aspergillus nidulans*.

3. A modified *Aspergillus nidulans* cell for producing penicillin, wherein said cell is transformed with a polynucleotide encoding a mutant IPNS consisting of the amino acid sequence SEQ ID NO:1, wherein said mutant continues to have IPNS activity but is dependent on bicarbonate as an activator in producing penicillin.

* * * * *

UNITED STATES PATENT AND TRADEMARK OFFICE
CERTIFICATE OF CORRECTION

PATENT NO. : 7,029,888 B2  Page 1 of 1
APPLICATION NO. : 09/924841
DATED : April 18, 2006
INVENTOR(S) : David R. Dilley et al.

It is certified that error appears in the above-identified patent and that said Letters Patent is hereby corrected as shown below:

On the title page, item (57),
Abstract, line 20, "enzyme either in either an" should be --enzyme either in an--.

Column 1, line 60, "phenyacetic" should be --phenylacetic--.

Column 3, line 55, "phenyacetic" should be --phenylacetic--.

Column 13, line 51, "DAOCS, or DAOCS can be" should be --DAOCS, or DAOCS/DACScan be--.

Column 14, line 45, "Goenen et al" should be --Groenen et al--.

Column 22, line 47, "to construed" should be --to be construed--.

Signed and Sealed this

Fourteenth Day of August, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 331
<212> TYPE: PRT
<213> ORGANISM: Artificial Sequence
<220> FEATURE:
<223> OTHER INFORMATION: Description of Artificial Sequence: modified
    IPNS from Emericella nidulans strain b1A1
<221> NAME/KEY: MUTAGEN
<222> LOCATION: (212)
<223> OTHER INFORMATION: Glu212 in native IPNS modified to Arg

<400> SEQUENCE: 1

```
Met Gly Ser Val Ser Lys Ala Asn Val Pro Lys Ile Asp Val Ser Pro
  1               5                  10                  15

Leu Phe Gly Asp Asp Gln Ala Ala Lys Met Arg Val Ala Gln Gln Ile
             20                  25                  30

Asp Ala Ala Ser Arg Asp Thr Gly Phe Phe Tyr Ala Val Asn His Gly
         35                  40                  45

Ile Asn Val Gln Arg Leu Ser Gln Lys Thr Lys Glu Phe His Met Ser
     50                  55                  60

Ile Thr Pro Glu Glu Lys Trp Asp Leu Ala Ile Arg Ala Tyr Asn Lys
 65                  70                  75                  80

Glu His Gln Asp Gln Val Arg Ala Gly Tyr Tyr Leu Ser Ile Pro Gly
                 85                  90                  95

Lys Lys Ala Val Glu Ser Phe Cys Tyr Leu Asn Pro Asn Phe Thr Pro
            100                 105                 110

Asp His Pro Arg Ile Gln Ala Lys Thr Pro Thr His Glu Val Asn Val
        115                 120                 125

Trp Pro Asp Glu Thr Lys His Pro Gly Phe Gln Asp Phe Ala Glu Gln
130                 135                 140

Tyr Tyr Trp Asp Val Phe Gly Leu Ser Ser Ala Leu Leu Lys Gly Tyr
145                 150                 155                 160

Ala Leu Ala Leu Gly Lys Glu Glu Asn Phe Phe Ala Arg His Phe Lys
                165                 170                 175

Pro Asp Asp Thr Leu Ala Ser Val Val Leu Ile Arg Tyr Pro Tyr Leu
            180                 185                 190

Asp Pro Tyr Pro Glu Ala Ala Ile Lys Thr Ala Ala Asp Gly Thr Lys
        195                 200                 205

Leu Ser Phe Arg Trp His Glu Asp Val Ser Leu Ile Thr Val Leu Tyr
210                 215                 220

Gln Ser Asn Val Gln Asn Leu Gln Val Glu Thr Ala Ala Gly Tyr Gln
225                 230                 235                 240

Asp Ile Glu Ala Asp Asp Thr Gly Tyr Leu Ile Asn Cys Gly Ser Tyr
                245                 250                 255

Met Ala His Leu Thr Asn Asn Tyr Tyr Lys Ala Pro Ile His Arg Val
            260                 265                 270

Lys Trp Val Asn Ala Glu Arg Gln Ser Leu Pro Phe Phe Val Asn Leu
        275                 280                 285

Gly Tyr Asp Ser Val Ile Asp Pro Phe Asp Pro Arg Glu Pro Asn Gly
    290                 295                 300

Lys Ser Asp Arg Glu Pro Leu Ser Tyr Gly Asp Tyr Leu Gln Asn Gly
305                 310                 315                 320

Leu Val Ser Leu Ile Asn Lys Asn Gly Gln Thr
```

```
<210> SEQ ID NO 2
<211> LENGTH: 331
<212> TYPE: PRT
<213> ORGANISM: Artificial Sequence
<220> FEATURE:
<223> OTHER INFORMATION: Description of Artificial Sequence:modified
      IPNS from Emericella nidulans strain FGSC-4
<221> NAME/KEY: MUTAGEN
<222> LOCATION: (212)
<223> OTHER INFORMATION: Glu212 in native IPNS modified to Arg

<400> SEQUENCE: 2

Met Gly Ser Val Ser Lys Ala Asn Val Pro Lys Ile Asp Val Ser Pro
  1               5                  10                  15

Leu Phe Gly Asp Asp Gln Ala Ala Lys Met Arg Val Ala Gln Gln Ile
             20                  25                  30

Asp Ala Ala Ser Arg Asp Thr Gly Phe Phe Tyr Ala Val Asn His Gly
         35                  40                  45

Ile Asn Val Gln Arg Leu Ser Gln Lys Thr Lys Glu Phe His Met Ser
 50                  55                  60

Ile Thr Pro Glu Glu Lys Trp Asp Leu Ala Ile Arg Ala Tyr Asn Lys
 65                  70                  75                  80

Glu His Gln Asp Gln Val Arg Ala Gly Tyr Tyr Leu Ser Ile Pro Gly
                 85                  90                  95

Lys Lys Ala Val Glu Ser Phe Cys Tyr Leu Asn Pro Asn Phe Thr Pro
            100                 105                 110

Asp His Pro Arg Ile Gln Ala Lys Thr Pro Thr His Glu Val Asn Val
        115                 120                 125

Trp Pro Asp Glu Thr Lys His Pro Gly Phe Gln Asp Phe Ala Glu Gln
130                 135                 140

Tyr Tyr Trp Asp Val Phe Gly Leu Ser Ser Ala Leu Leu Lys Gly Tyr
145                 150                 155                 160

Ala Leu Ala Leu Gly Lys Glu Glu Asn Phe Phe Ala Arg His Phe Lys
                165                 170                 175

Pro Asp Asp Thr Leu Ala Ser Val Val Leu Ile Arg Tyr Pro Tyr Leu
            180                 185                 190

Asp Pro Tyr Pro Glu Ala Ala Ile Lys Thr Ala Ala Asp Gly Thr Lys
        195                 200                 205

Leu Ser Phe Arg Trp His Glu Asp Val Ser Leu Ile Thr Val Leu Tyr
210                 215                 220

Gln Ser Asn Val Gln Asn Leu Gln Val Glu Thr Ala Ala Gly Tyr Gln
225                 230                 235                 240

Asp Ile Glu Ala Asp Asp Thr Gly Tyr Leu Ile Asn Cys Gly Ser Tyr
                245                 250                 255

Met Ala His Leu Thr Asn Asn Tyr Tyr Lys Ala Pro Ile His Arg Val
            260                 265                 270

Lys Trp Val Asn Ala Glu Arg Gln Ser Leu Pro Phe Phe Val Asn Leu
        275                 280                 285

Gly Tyr Asp Ser Val Ile Asp Pro Phe Asp Pro Arg Glu Pro Asn Gly
    290                 295                 300

Lys Ser Asp Arg Glu Pro Leu Ser Tyr Gly Asp Tyr Leu Gln Asn Gly
305                 310                 315                 320

Leu Val Ser Leu Ile Asn Lys Asn Gly Gln Thr
                325                 330
```

```
<210> SEQ ID NO 3
<211> LENGTH: 331
<212> TYPE: PRT
<213> ORGANISM: Artificial Sequence
<220> FEATURE:
<223> OTHER INFORMATION: Description of Artificial Sequence: modified
      IPNS from Emericella nidulans strain bioA1
<221> NAME/KEY: MUTAGEN
<222> LOCATION: (212)
<223> OTHER INFORMATION: Glu212 in native IPNS modified to Arg

<400> SEQUENCE: 3

Met Gly Ser Val Ser Lys Ala Asn Val Pro Lys Ile Asp Val Ser Pro
  1               5                  10                  15

Leu Phe Gly Asp Asp Gln Ala Ala Lys Met Arg Val Ala Gln Gln Ile
                 20                  25                  30

Asp Ala Ala Ser Arg Asp Thr Gly Phe Phe Tyr Ala Val Asn His Gly
             35                  40                  45

Ile Asn Val Gln Arg Leu Ser Gln Lys Thr Lys Glu Phe His Met Ser
 50                  55                  60

Ile Thr Pro Glu Glu Lys Trp Asp Leu Ala Ile Arg Ala Tyr Asn Lys
 65                  70                  75                  80

Glu His Gln Asp Gln Val Arg Ala Gly Tyr Tyr Leu Ser Ile Pro Gly
                 85                  90                  95

Lys Lys Ala Val Glu Ser Phe Cys Tyr Leu Asn Pro Asn Phe Thr Pro
            100                 105                 110

Asp His Pro Arg Ile Gln Ala Lys Thr Pro Thr His Glu Val Asn Val
            115                 120                 125

Trp Pro Asp Glu Thr Lys His Pro Gly Phe Gln Asp Phe Ala Glu Gln
130                 135                 140

Tyr Tyr Trp Asp Val Phe Gly Leu Ser Ser Ala Leu Leu Lys Gly Tyr
145                 150                 155                 160

Ala Leu Ala Leu Gly Lys Glu Glu Asn Phe Phe Ala Arg His Phe Lys
                165                 170                 175

Pro Asp Asp Thr Leu Ala Ser Val Val Leu Ile Arg Tyr Pro Tyr Leu
            180                 185                 190

Asp Pro Tyr Pro Glu Ala Ala Ile Lys Thr Ala Ala Asp Gly Thr Lys
            195                 200                 205

Leu Ser Phe Arg Trp His Glu Asp Val Ser Leu Ile Thr Val Leu Tyr
210                 215                 220

Gln Ser Asn Val Gln Asn Leu Gln Val Glu Thr Ala Ala Gly Tyr Gln
225                 230                 235                 240

Asp Ile Glu Ala Asp Asp Thr Gly Tyr Leu Ile Asn Cys Gly Ser Tyr
                245                 250                 255

Met Ala His Leu Thr Asn Asn Tyr Tyr Lys Ala Pro Ile His Arg Val
            260                 265                 270

Lys Trp Val Asn Ala Glu Arg Gln Ser Leu Pro Phe Phe Val Asn Leu
            275                 280                 285

Gly Tyr Asp Ser Val Ile Asp Pro Phe Asp Pro Arg Glu Pro Asn Gly
290                 295                 300

Lys Ser Asp Arg Glu Pro Leu Ser Tyr Gly Asp Tyr Leu Gln Asn Gly
305                 310                 315                 320

Leu Val Ser Leu Ile Asn Lys Asn Gly Gln Thr
                325                 330

<210> SEQ ID NO 4
```

```
<211> LENGTH: 331
<212> TYPE: PRT
<213> ORGANISM: Artificial Sequence
<220> FEATURE:
<223> OTHER INFORMATION: Description of Artificial Sequence: modified
      IPNS from Penicillium chrysogenum
<221> NAME/KEY: MUTAGEN
<222> LOCATION: (212)
<223> OTHER INFORMATION: Glu212 in native IPNS modified to Arg

<400> SEQUENCE: 4
```

Met Ala Ser Thr Pro Lys Ala Asn Val Pro Lys Ile Asp Val Ser Pro
 1               5                  10                  15

Leu Phe Gly Asp Asn Met Glu Glu Lys Met Lys Val Ala Arg Ala Ile
            20                  25                  30

Asp Ala Ala Ser Arg Asp Thr Gly Phe Phe Tyr Ala Val Asn His Gly
        35                  40                  45

Val Asp Val Lys Arg Leu Ser Asn Lys Thr Arg Glu Phe His Phe Ser
    50                  55                  60

Ile Thr Asp Glu Glu Lys Trp Asp Leu Ala Ile Arg Ala Tyr Asn Lys
 65                  70                  75                  80

Glu His Gln Asp Gln Ile Arg Ala Gly Tyr Tyr Leu Ser Ile Pro Glu
                85                  90                  95

Lys Lys Ala Val Glu Ser Phe Cys Tyr Leu Asn Pro Asn Phe Lys Pro
            100                 105                 110

Asp His Pro Leu Ile Gln Ser Lys Thr Pro Thr His Glu Val Asn Val
        115                 120                 125

Trp Pro Asp Glu Lys Lys His Pro Gly Phe Arg Glu Phe Ala Glu Gln
    130                 135                 140

Tyr Tyr Trp Asp Val Phe Gly Leu Ser Ser Ala Leu Leu Arg Gly Tyr
145                 150                 155                 160

Ala Leu Ala Leu Gly Lys Glu Glu Asp Phe Phe Ser Arg His Phe Lys
                165                 170                 175

Lys Glu Asp Ala Leu Ser Ser Val Val Leu Ile Arg Tyr Pro Tyr Leu
            180                 185                 190

Asn Pro Ile Pro Pro Ala Ala Ile Lys Thr Ala Glu Asp Gly Thr Lys
        195                 200                 205

Leu Ser Phe Arg Trp His Glu Asp Val Ser Leu Ile Thr Val Leu Tyr
    210                 215                 220

Gln Ser Asp Val Ala Asn Leu Gln Val Glu Met Pro Gln Gly Tyr Leu
225                 230                 235                 240

Asp Ile Glu Ala Asp Asp Asn Ala Tyr Leu Val Asn Cys Gly Ser Tyr
                245                 250                 255

Met Ala His Ile Thr Asn Asn Tyr Tyr Pro Ala Pro Ile His Arg Val
            260                 265                 270

Lys Trp Val Asn Glu Glu Arg Gln Ser Leu Pro Phe Phe Val Asn Leu
        275                 280                 285

Gly Phe Asn Asp Thr Val Gln Pro Trp Asp Pro Ser Lys Glu Asp Gly
    290                 295                 300

Lys Thr Asp Gln Arg Pro Ile Ser Tyr Gly Asp Tyr Leu Gln Asn Gly
305                 310                 315                 320

Leu Val Ser Leu Ile Asn Lys Asn Gly Gln Thr
                325                 330

```
<210> SEQ ID NO 5
<211> LENGTH: 329
<212> TYPE: PRT
```

<213> ORGANISM: Artificial Sequence
<220> FEATURE:
<223> OTHER INFORMATION: Description of Artificial Sequence: modified
     IPNS from Streptomyces clavuligerus
<221> NAME/KEY: MUTAGEN
<222> LOCATION: (210)
<223> OTHER INFORMATION: Glu210 in native IPNS modified to Arg

<400> SEQUENCE: 5

Met Pro Val Leu Met Pro Ser Ala His Val Pro Thr Ile Asp Ile Ser
 1               5                  10                  15

Pro Leu Phe Gly Thr Asp Ala Ala Lys Lys Arg Val Ala Glu Glu
            20                  25                  30

Ile His Gly Ala Cys Arg Gly Ser Gly Phe Phe Tyr Ala Thr Asn His
        35                  40                  45

Gly Val Asp Val Gln Gln Leu Gln Asp Val Val Asn Glu Phe His Gly
     50                  55                  60

Ala Met Thr Asp Gln Glu Lys His Asp Leu Ala Ile His Ala Tyr Asn
 65                  70                  75                  80

Pro Asp Asn Pro His Val Arg Asn Gly Tyr Tyr Lys Ala Val Pro Gly
                85                  90                  95

Arg Lys Ala Val Glu Ser Phe Cys Tyr Leu Asn Pro Asp Phe Gly Glu
            100                 105                 110

Asp His Pro Met Ile Ala Ala Gly Thr Pro Met His Glu Val Asn Leu
        115                 120                 125

Trp Pro Asp Glu Glu Arg His Pro Arg Phe Arg Pro Phe Cys Glu Gly
130                 135                 140

Tyr Tyr Arg Gln Met Leu Lys Leu Ser Thr Val Leu Met Arg Gly Leu
145                 150                 155                 160

Ala Leu Ala Leu Gly Arg Pro Glu His Phe Phe Asp Ala Ala Leu Ala
                165                 170                 175

Glu Gln Asp Ser Leu Ser Ser Val Ser Leu Ile Arg Tyr Pro Tyr Leu
            180                 185                 190

Glu Glu Tyr Pro Pro Val Lys Thr Gly Pro Asp Gly Gln Leu Leu Ser
        195                 200                 205

Phe Arg Asp His Leu Asp Val Ser Met Ile Thr Val Leu Phe Gln Thr
210                 215                 220

Gln Val Gln Asn Leu Gln Val Glu Thr Val Asp Gly Trp Arg Asp Ile
225                 230                 235                 240

Pro Thr Ser Glu Asn Asp Phe Leu Val Asn Cys Gly Thr Tyr Met Ala
                245                 250                 255

His Val Thr Asn Asp Tyr Phe Pro Ala Pro Asn His Arg Val Lys Phe
            260                 265                 270

Val Asn Ala Glu Arg Leu Ser Leu Pro Phe Phe Leu Asn Gly Gly His
        275                 280                 285

Glu Ala Val Ile Glu Pro Phe Val Pro Glu Gly Ala Ser Glu Glu Val
    290                 295                 300

Arg Asn Glu Ala Leu Ser Tyr Gly Asp Tyr Leu Gln His Gly Leu Arg
305                 310                 315                 320

Ala Leu Ile Val Lys Asn Gly Gln Thr
                325

<210> SEQ ID NO 6
<211> LENGTH: 338
<212> TYPE: PRT
<213> ORGANISM: Artificial Sequence
<220> FEATURE:

<223> OTHER INFORMATION: Description of Artificial Sequence: modified
      IPNS from Acremonium chrysogenum
<221> NAME/KEY: MUTAGEN
<222> LOCATION: (214)
<223> OTHER INFORMATION: Glu214 in native IPNS modified to Arg

<400> SEQUENCE: 6

```
Met Gly Ser Val Pro Val Pro Val Ala Asn Val Pro Arg Ile Asp Val
 1               5                  10                  15

Ser Pro Leu Phe Gly Asp Asp Lys Glu Lys Lys Leu Glu Val Ala Arg
            20                  25                  30

Ala Ile Asp Ala Ala Ser Arg Asp Thr Gly Phe Phe Tyr Ala Val Asn
         35                  40                  45

His Gly Val Asp Leu Pro Trp Leu Ser Arg Glu Thr Asn Lys Phe His
     50                  55                  60

Met Ser Ile Thr Asp Glu Glu Lys Trp Gln Leu Ala Ile Arg Ala Tyr
 65                  70                  75                  80

Asn Lys Glu His Glu Ser Gln Ile Arg Ala Gly Tyr Tyr Leu Pro Ile
                 85                  90                  95

Pro Gly Lys Lys Ala Val Glu Ser Phe Cys Tyr Leu Asn Pro Ser Phe
            100                 105                 110

Ser Pro Asp His Pro Arg Ile Lys Glu Pro Thr Pro Met His Glu Val
        115                 120                 125

Asn Val Trp Pro Asp Glu Ala Lys His Pro Gly Phe Arg Ala Phe Ala
130                 135                 140

Glu Lys Tyr Tyr Trp Asp Val Phe Gly Leu Ser Ser Ala Val Leu Arg
145                 150                 155                 160

Gly Tyr Ala Leu Ala Leu Gly Arg Asp Glu Asp Phe Phe Thr Arg His
                165                 170                 175

Ser Arg Arg Asp Thr Thr Leu Ser Ser Val Val Leu Ile Arg Tyr Pro
            180                 185                 190

Tyr Leu Asp Pro Tyr Pro Glu Pro Ala Ile Lys Thr Ala Asp Asp Gly
        195                 200                 205

Thr Lys Leu Ser Phe Arg Trp His Glu Asp Val Ser Leu Ile Thr Val
210                 215                 220

Leu Tyr Gln Ser Asp Val Gln Asn Leu Gln Val Lys Thr Pro Gln Gly
225                 230                 235                 240

Trp Gln Asp Ile Gln Ala Asp Asp Thr Gly Phe Leu Ile Asn Cys Gly
                245                 250                 255

Ser Tyr Met Ala His Ile Thr Asp Tyr Tyr Pro Ala Pro Ile His
            260                 265                 270

Arg Val Lys Trp Val Asn Glu Glu Arg Gln Ser Leu Pro Phe Phe Val
        275                 280                 285

Asn Leu Gly Trp Glu Asp Thr Ile Gln Pro Trp Asp Pro Ala Thr Ala
290                 295                 300

Lys Asp Gly Ala Lys Asp Ala Ala Lys Asp Lys Pro Ala Ile Ser Tyr
305                 310                 315                 320

Gly Glu Tyr Leu Gln Gly Gly Leu Arg Gly Leu Ile Asn Lys Asn Gly
                325                 330                 335

Gln Thr
```

<210> SEQ ID NO 7
<211> LENGTH: 338
<212> TYPE: PRT
<213> ORGANISM: Artificial Sequence
<220> FEATURE:

<223> OTHER INFORMATION: Description of Artificial Sequence: modified
     IPNS from Acremonium chrysogenum strain M8650
<221> NAME/KEY: MUTAGEN
<222> LOCATION: (214)
<223> OTHER INFORMATION: Glu214 in native IPNS modified to Arg

<400> SEQUENCE: 7

Met Gly Ser Val Pro Val Pro Val Ala Asn Val Pro Arg Ile Asp Val
 1               5                  10                  15

Ser Pro Leu Phe Gly Asp Asp Lys Glu Lys Leu Glu Val Ala Arg
             20                  25                  30

Ala Ile Asp Ala Ala Ser Arg Asp Thr Gly Phe Phe Tyr Ala Val Asn
         35                  40                  45

His Gly Val Asp Leu Pro Trp Leu Ser Arg Glu Thr Asn Lys Phe His
     50                  55                  60

Met Ser Ile Thr Asp Glu Glu Lys Trp Gln Leu Ala Ile Arg Ala Tyr
 65                  70                  75                  80

Asn Lys Glu His Glu Ser Gln Ile Arg Ala Gly Tyr Tyr Leu Pro Ile
                 85                  90                  95

Pro Gly Lys Lys Ala Val Glu Ser Phe Cys Tyr Leu Asn Pro Ser Phe
            100                 105                 110

Ser Pro Asp His Pro Arg Ile Lys Glu Pro Thr Pro Met His Glu Val
        115                 120                 125

Asn Val Trp Pro Asp Glu Ala Lys His Pro Gly Phe Arg Ala Phe Ala
130                 135                 140

Glu Lys Tyr Tyr Trp Asp Val Phe Gly Leu Ser Ser Ala Val Leu Arg
145                 150                 155                 160

Gly Tyr Ala Leu Ala Leu Gly Arg Asp Glu Asp Phe Phe Thr Arg His
                165                 170                 175

Phe Arg Arg Asp Thr Thr Leu Ser Ser Val Val Leu Ile Arg Tyr Pro
            180                 185                 190

Tyr Leu Asp Pro Tyr Pro Glu Pro Ala Ile Lys Thr Ala Asp Asp Gly
        195                 200                 205

Thr Lys Leu Ser Phe Arg Trp His Glu Asp Val Ser Leu Ile Thr Val
210                 215                 220

Leu Tyr Gln Ser Asp Val Gln Asn Leu Gln Val Lys Thr Pro Gln Gly
225                 230                 235                 240

Trp Gln Asp Ile Gln Ala Asp Asp Thr Gly Phe Leu Ile Asn Cys Gly
                245                 250                 255

Ser Tyr Met Ala His Ile Thr Asp Tyr Tyr Pro Ala Pro Ile His
            260                 265                 270

Arg Val Lys Trp Val Asn Glu Glu Arg Gln Ser Leu Pro Phe Phe Val
        275                 280                 285

Asn Leu Gly Trp Glu Asp Thr Ile Gln Pro Trp Asp Pro Ala Thr Ala
290                 295                 300

Lys Asp Gly Ala Lys Asp Ala Ala Lys Asp Lys Pro Ala Ile Ser Tyr
305                 310                 315                 320

Gly Glu Tyr Leu Gln Gly Gly Leu Arg Gly Leu Ile Asn Lys Asn Gly
                325                 330                 335

Gln Thr

<210> SEQ ID NO 8
<211> LENGTH: 321
<212> TYPE: PRT
<213> ORGANISM: Artificial Sequence
<220> FEATURE:

```
<223> OTHER INFORMATION: Description of Artificial Sequence: modified
      IPNS from Streptomyces cattleya
<221> NAME/KEY: MUTAGEN
<222> LOCATION: (211)
<223> OTHER INFORMATION: Glu211 in native IPNS modified to Arg

<400> SEQUENCE: 8

Met Pro Val Leu Met Pro Ser Ala Asp Val Pro Thr Ile Asp Ile Ser
 1               5                  10                  15

Pro Gln Leu Phe Gly Thr Asp Pro Thr Pro Arg Arg Thr Ser Arg Gly
                20                  25                  30

Arg Ser Thr Arg Pro Ala Arg Gly Ser Gly Phe Phe Tyr Ala Ser His
            35                  40                  45

His Gly Ile Asp Val Arg Arg Leu Gln Thr Trp Ser Asn Glu Ser Thr
        50                  55                  60

Thr Met Thr Asp Gln Arg Ser Thr Thr Trp Arg Ser Thr Arg Tyr Asn
65                  70                  75                  80

Glu Asn Asn Ser His Val Arg Asn Gly Tyr Tyr Met Ala Arg Pro Gly
                85                  90                  95

Arg Glu Thr Val Glu Ser Trp Cys Tyr Leu Asn Pro Ser Phe Gly Glu
            100                 105                 110

Asp His Pro Met Met Lys Ala Gly Thr Pro Met His Glu Val Asn Val
        115                 120                 125

Trp Pro Asp Glu Glu Arg His Pro Asp Phe Gly Ser Phe Gly Glu Gln
    130                 135                 140

Tyr His Arg Glu Val Ser Ala Ser Arg Arg Cys Cys Cys Gly Ala Ser
145                 150                 155                 160

Arg Trp Arg Arg Gln Ala Gly Glu Ser Ser Asn Glu Val Thr Glu
                165                 170                 175

Glu Asp Thr Leu Ser Ala Val Ser Met Ile Arg Tyr Pro Tyr Leu Asp
            180                 185                 190

Pro Tyr Pro Glu Ala Ala Ile Lys Thr Gly Pro Asp Gly Thr Arg Leu
        195                 200                 205

Ser Phe Arg Asp His Leu Asp Val Ser Met Ile Thr Val Leu Ser Lys
    210                 215                 220

Thr Glu Val Gln Asn Leu Gln Val Glu Thr Val Asp Gly Trp Gln Ser
225                 230                 235                 240

Leu Pro Thr Ser Gly Glu Asn Phe Leu Ile Asn Cys Gly Thr Tyr Leu
                245                 250                 255

Gly Tyr Leu Thr Asn Asp Tyr Phe Pro Ala Pro Asn His Arg Val Lys
            260                 265                 270

Tyr Val Asn Ala Glu Arg Leu Ser Leu Pro Phe Phe Leu His Ala Gly
        275                 280                 285

Gln Asn Ser Val Met Lys Pro Phe Thr Arg Arg Thr Gly Asp Arg Lys
    290                 295                 300

Leu Asn Pro Ala Val Thr Tyr Gly Glu Tyr Leu Gln Glu Gly Phe Thr
305                 310                 315                 320

Arg

<210> SEQ ID NO 9
<211> LENGTH: 329
<212> TYPE: PRT
<213> ORGANISM: Artificial Sequence
<220> FEATURE:
<223> OTHER INFORMATION: Description of Artificial Sequence: modified
      IPNS from Streptomyces clavuligerus strain NRRL 3585
<221> NAME/KEY: MUTAGEN
```

<222> LOCATION: (210)
<223> OTHER INFORMATION: Glu210 in native IPNS modified to Arg

<400> SEQUENCE: 9

```
Met Pro Val Leu Met Pro Ser Ala His Val Pro Thr Ile Asp Ile Ser
 1               5                  10                  15
Pro Leu Phe Gly Thr Asp Ala Ala Lys Lys Arg Val Ala Glu Glu
             20                  25                  30
Ile His Gly Ala Cys Arg Gly Ser Gly Phe Phe Tyr Ala Thr Asn His
                 35                  40                  45
Gly Val Asp Val Gln Gln Leu Gln Asp Val Val Asn Glu Phe His Gly
 50                  55                  60
Ala Met Thr Asp Gln Glu Lys His Asp Leu Ala Ile His Ala Tyr Asn
 65                  70                  75                  80
Pro Asp Asn Pro His Val Arg Asn Gly Tyr Tyr Lys Ala Val Pro Gly
                     85                  90                  95
Arg Lys Ala Val Glu Ser Phe Cys Tyr Leu Asn Pro Asp Phe Gly Glu
                100                 105                 110
Asp His Pro Met Ile Ala Ala Gly Thr Pro Met His Glu Val Asn Leu
            115                 120                 125
Trp Pro Asp Glu Glu Arg His Pro Arg Phe Arg Pro Phe Cys Glu Gly
130                 135                 140
Tyr Tyr Arg Gln Met Leu Lys Leu Ser Thr Val Leu Met Arg Gly Leu
145                 150                 155                 160
Ala Leu Ala Leu Gly Arg Pro Glu His Phe Phe Asp Ala Ala Leu Ala
                165                 170                 175
Glu Gln Asp Ser Leu Ser Ser Val Ser Leu Ile Arg Tyr Pro Tyr Leu
                180                 185                 190
Glu Glu Tyr Pro Pro Val Lys Thr Gly Pro Asp Gly Gln Leu Leu Ser
            195                 200                 205
Phe Arg Asp His Leu Asp Val Ser Met Ile Thr Val Leu Phe Gln Thr
210                 215                 220
Gln Val Gln Asn Leu Gln Val Glu Thr Val Asp Gly Trp Arg Asp Ile
225                 230                 235                 240
Pro Thr Ser Glu Asn Asp Phe Leu Val Asn Cys Gly Thr Tyr Met Ala
                245                 250                 255
His Val Thr Asn Asp Tyr Phe Pro Ala Pro Asn His Arg Val Lys Phe
                260                 265                 270
Val Asn Ala Glu Arg Leu Ser Leu Pro Phe Phe Leu Asn Gly Gly His
            275                 280                 285
Glu Ala Val Ile Glu Pro Phe Val Pro Glu Gly Ala Ser Glu Glu Val
290                 295                 300
Arg Asn Glu Ala Leu Ser Tyr Gly Asp Tyr Leu Gln His Gly Leu Arg
305                 310                 315                 320
Ala Leu Ile Val Lys Asn Gly Gln Thr
                325
```

<210> SEQ ID NO 10
<211> LENGTH: 333
<212> TYPE: PRT
<213> ORGANISM: Artificial Sequence
<220> FEATURE:
<223> OTHER INFORMATION: Description of Artificial Sequence: modified
      IPNS from streptomyces anulatus ( S. lipmanii)
<221> NAME/KEY: MUTAGEN
<222> LOCATION: (214)
<223> OTHER INFORMATION: Glu214 in native IPNS modified to Arg

<400> SEQUENCE: 10

```
Met Pro Val Leu Met Pro Ser Ala Asp Val Pro Thr Ile Asp Ile Ser
 1               5                  10                  15

Pro Leu Phe Gly Thr Asp Pro Asp Ala Lys Ala His Val Ala Arg Gln
                20                  25                  30

Ile Asn Glu Ala Cys Arg Gly Ser Gly Phe Phe Tyr Ala Ser His His
            35                  40                  45

Gly Ile Asp Val Arg Arg Leu Gln Asp Val Val Asn Glu Phe His Arg
50                  55                  60

Thr Met Thr Asp Gln Glu Lys His Asp Leu Ala Ile His Ala Tyr Asn
65                  70                  75                  80

Glu Asn Asn Ser His Val Arg Asn Gly Tyr Tyr Met Ala Arg Pro Gly
                85                  90                  95

Arg Lys Thr Val Glu Ser Trp Cys Tyr Leu Asn Pro Ser Phe Gly Glu
            100                 105                 110

Asp His Pro Met Ile Lys Ala Gly Thr Pro Met His Glu Val Asn Val
            115                 120                 125

Trp Pro Asp Glu Glu Arg His Pro Asp Phe Arg Ser Phe Gly Glu Gln
130                 135                 140

Tyr Tyr Arg Glu Val Phe Arg Leu Ser Lys Val Leu Leu Leu Arg Gly
145                 150                 155                 160

Phe Ala Leu Ala Leu Gly Lys Pro Glu Glu Phe Phe Glu Asn Glu Val
                165                 170                 175

Thr Glu Glu Asp Thr Leu Ser Cys Arg Ser Leu Met Ile Arg Tyr Pro
            180                 185                 190

Tyr Leu Asp Pro Tyr Pro Glu Ala Ala Ile Lys Thr Gly Pro Asp Gly
            195                 200                 205

Thr Arg Leu Ser Phe Arg Asp His Leu Asp Val Ser Met Ile Thr Val
210                 215                 220

Leu Phe Gln Thr Glu Val Gln Asn Leu Gln Val Glu Thr Val Asp Gly
225                 230                 235                 240

Trp Gln Ser Leu Pro Thr Ser Gly Glu Asn Phe Leu Ile Asn Cys Gly
                245                 250                 255

Thr Tyr Leu Gly Tyr Leu Thr Asn Asp Tyr Phe Pro Ala Pro Asn His
            260                 265                 270

Arg Val Lys Tyr Val Asn Ala Glu Arg Leu Ser Leu Pro Phe Phe Leu
            275                 280                 285

His Ala Gly Gln Asn Ser Val Met Lys Pro Phe His Pro Glu Asp Thr
290                 295                 300

Gly Asp Arg Lys Leu Asn Pro Ala Val Thr Tyr Gly Glu Tyr Leu Gln
305                 310                 315                 320

Glu Gly Phe His Ala Leu Ile Ala Lys Asn Val Gln Thr
                325                 330
```

<210> SEQ ID NO 11
<211> LENGTH: 21
<212> TYPE: PRT
<213> ORGANISM: Emericella nidulans
<220> FEATURE:
<221> NAME/KEY: PEPTIDE
<222> LOCATION: (1)..(21)
<223> OTHER INFORMATION: corresponds to amino acids 205 to 225 of native IPNS

<400> SEQUENCE: 11

```
Asp Gly Thr Lys Leu Ser Phe Glu Trp His Glu Asp Val Ser Leu Ile
 1               5                  10                  15

Thr Val Leu Tyr Gln
            20

<210> SEQ ID NO 12
<211> LENGTH: 21
<212> TYPE: PRT
<213> ORGANISM: Penicillium chrysogenum
<220> FEATURE:
<221> NAME/KEY: PEPTIDE
<222> LOCATION: (1)..(21)
<223> OTHER INFORMATION: corresponds to amino acids 205 to 225 of
      native IPNS

<400> SEQUENCE: 12

Asp Gly Thr Lys Leu Ser Phe Glu Trp His Glu Asp Val Ser Leu Ile
 1               5                  10                  15

Thr Val Leu Tyr Gln
            20

<210> SEQ ID NO 13
<211> LENGTH: 21
<212> TYPE: PRT
<213> ORGANISM: Acremonium chrysogenum
<220> FEATURE:
<221> NAME/KEY: PEPTIDE
<222> LOCATION: (1)..(21)
<223> OTHER INFORMATION: corresponds to amino acids 207 to ss7 of
      native IPNS

<400> SEQUENCE: 13

Asp Gly Thr Lys Leu Ser Phe Glu Trp His Glu Asp Val Ser Leu Ile
 1               5                  10                  15

Thr Val Leu Tyr Gln
            20

<210> SEQ ID NO 14
<211> LENGTH: 21
<212> TYPE: PRT
<213> ORGANISM: Streptomyces clavuligerus
<220> FEATURE:
<221> NAME/KEY: PEPTIDE
<222> LOCATION: (1)..(21)
<223> OTHER INFORMATION: corresponds to amino acids 302 to 223 of
      native IPNS

<400> SEQUENCE: 14

Asp Gly Gln Leu Leu Ser Phe Glu Asp His Leu Asp Val Ser Met Ile
 1               5                  10                  15

Thr Val Leu Phe Gln
            20

<210> SEQ ID NO 15
<211> LENGTH: 21
<212> TYPE: PRT
<213> ORGANISM: Streptomyces cattleya
<220> FEATURE:
<221> NAME/KEY: PEPTIDE
<222> LOCATION: (1)..(21)
<223> OTHER INFORMATION: corresponds to amino acids 204 to 224 of
      native IPNS

<400> SEQUENCE: 15

Asp Gly Thr Arg Leu Ser Phe Glu Asp His Leu Asp Val Ser Met Ile
 1               5                  10                  15
```

Thr Val Leu Ser Glu
            20

<210> SEQ ID NO 16
<211> LENGTH: 21
<212> TYPE: PRT
<213> ORGANISM: Streptomyces anulatus
<220> FEATURE:
<221> NAME/KEY: PEPTIDE
<222> LOCATION: (1)..(21)
<223> OTHER INFORMATION: corresponds to amino acids 207 to 227 of
      native IPNS

<400> SEQUENCE: 16

Asp Gly Thr Arg Leu Ser Phe Glu Asp His Leu Asp Val Ser Met Ile
 1               5                  10                  15

Thr Val Leu Phe Gln
            20

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: mutagenic
      oligonucleotide primer

<400> SEQUENCE: 17
ctgagttttg agtggcatcg ggatgtaatc                                           30

<210> SEQ ID NO 18
<211> LENGTH: 311
<212> TYPE: PRT
<213> ORGANISM: Artificial Sequence
<220> FEATURE:
<223> OTHER INFORMATION: Description of Artificial Sequence: modified
      DAOCS from Streptomyces clavuligerus
<221> NAME/KEY: MUTAGEN
<222> LOCATION: (181)
<223> OTHER INFORMATION: Ala181 in native DAOCS modified to Arg

<400> SEQUENCE: 18

Met Asp Thr Thr Val Pro Thr Phe Ser Leu Ala Glu Leu Gln Gln Gly
 1               5                  10                  15

Leu His Gln Asp Glu Phe Arg Arg Cys Leu Arg Asp Lys Gly Leu Phe
            20                  25                  30

Tyr Leu Thr Asp Cys Gly Leu Thr Asp Thr Glu Leu Lys Ser Ala Lys
        35                  40                  45

Asp Leu Val Ile Asp Phe Phe Glu His Gly Ser Glu Ala Glu Lys Arg
    50                  55                  60

Ala Val Thr Ser Pro Val Pro Thr Met Arg Arg Gly Phe Thr Gly Leu
65                  70                  75                  80

Glu Ser Glu Ser Thr Ala Gln Ile Thr Asn Thr Gly Ser Tyr Ser Asp
                85                  90                  95

Tyr Ser Met Cys Tyr Ser Met Gly Thr Ala Asp Asn Leu Phe Pro Ser
            100                 105                 110

Gly Asp Phe Glu Arg Ile Trp Thr Gln Tyr Phe Asp Arg Gln Tyr Thr
        115                 120                 125

Ala Ser Arg Ala Val Ala Arg Glu Val Leu Arg Ala Thr Gly Thr Glu
    130                 135                 140

Pro Asp Gly Gly Val Glu Ala Phe Leu Asp Cys Glu Pro Leu Leu Arg
145                 150                 155                 160

-continued

```
Phe Arg Tyr Phe Pro Gln Val Pro Glu His Arg Ser Ala Glu Glu Gln
            165                 170                 175
Pro Leu Arg Met Arg Pro His Tyr Asp Leu Ser Met Val Thr Leu Ile
            180                 185                 190
Gln Gln Thr Pro Cys Ala Asn Gly Phe Val Ser Leu Gln Ala Glu Val
        195                 200                 205
Gly Gly Ala Phe Thr Asp Leu Pro Tyr Arg Pro Asp Ala Val Leu Val
    210                 215                 220
Phe Cys Gly Ala Ile Ala Thr Leu Val Thr Gly Gly Gln Val Lys Ala
225                 230                 235                 240
Pro Arg His His Val Ala Ala Pro Arg Arg Asp Gln Ile Ala Gly Ser
            245                 250                 255
Ser Arg Thr Ser Ser Val Phe Phe Leu Arg Pro Asn Ala Asp Phe Thr
            260                 265                 270
Phe Ser Val Pro Leu Ala Arg Glu Cys Gly Phe Asp Val Ser Leu Asp
            275                 280                 285
Gly Glu Thr Ala Thr Phe Gln Asp Trp Ile Gly Gly Asn Tyr Val Asn
    290                 295                 300
Ile Arg Arg Thr Ser Lys Ala
305                 310
```